(12) United States Patent
Bloom et al.

(10) Patent No.: US 8,864,791 B2
(45) Date of Patent: Oct. 21, 2014

(54) CATHETER SYSTEMS AND METHODS OF USE

(75) Inventors: Eliot Frank Bloom, Hopkinton, NH (US); Donald Earles, Exeter, NH (US)

(73) Assignee: John R. Roberts, Brentwood, TN (US)

( * ) Notice: Subject to any disclaimer, the term of this patent is extended or adjusted under 35 U.S.C. 154(b) by 99 days.

(21) Appl. No.: 13/227,273

(22) Filed: Sep. 7, 2011

(65) Prior Publication Data
US 2012/0259208 A1      Oct. 11, 2012

Related U.S. Application Data

(63) Continuation-in-part of application No. 13/083,462, filed on Apr. 8, 2011.

(51) Int. Cl.
| | |
|---|---|
| *A61M 29/00* | (2006.01) |
| *A61M 25/00* | (2006.01) |
| *A61M 16/04* | (2006.01) |
| *A61M 16/08* | (2006.01) |
| *A61M 25/04* | (2006.01) |
| *A61M 25/01* | (2006.01) |

(52) U.S. Cl.
CPC ....... *A61M 25/0097* (2013.01); *A61M 16/0463* (2013.01); *A61M 25/0032* (2013.01); *A61M 16/0488* (2013.01); *A61M 16/0816* (2013.01); *A61M 16/0833* (2013.01); *A61M 16/0418* (2013.01); *A61M 16/0484* (2013.01); *A61M 16/0486* (2013.01); *A61M 25/0041* (2013.01); *A61M 25/04* (2013.01); *A61M 2025/0037* (2013.01); *A61M 2025/0175* (2013.01); *A61M 16/0434* (2013.01); *A61M 2205/32* (2013.01); *A61M 2205/3375* (2013.01); *A61M 2205/583* (2013.01); *A61M 2205/6045* (2013.01)
USPC ....................................................... 606/200

(58) Field of Classification Search
CPC ........... A61B 8/12; A61B 2018/00952; A61B 7/003; A61M 16/0463; A61M 25/0041
USPC .......... 156/85, 304.02, 304.6; 604/284, 6.16; 29/447
See application file for complete search history.

(56) References Cited

U.S. PATENT DOCUMENTS

| | | | |
|---|---|---|---|
| 2,862,498 | A | 12/1958 | Weekes |
| 4,488,548 | A | 12/1984 | Agdanowski |

(Continued)

FOREIGN PATENT DOCUMENTS

| | | |
|---|---|---|
| WO | WO 2007/008332 A2 | 1/2007 |
| WO | WO 2008/032230 A1 | 3/2008 |
| WO | WO 2010/044051 A1 | 4/2010 |

OTHER PUBLICATIONS

International Search Report and Written Opinion for International Appl. No. PCT/US2011/062440, European Patent Office, The Netherlands, mailed on Jun. 11, 2012, 25 pages.

(Continued)

*Primary Examiner* — Elmer Chao
(74) *Attorney, Agent, or Firm* — Venable LLP; Michele V. Frank

(57) ABSTRACT

A catheter system can include a first catheter including a first proximal end portion and a lumen. The first proximal end portion has a first key joint component that extends along a partial length of the first proximal end portion. The catheter system can also include a second catheter including a second key joint component that corresponds with the first key joint component. The first key joint component and the second key joint component are configured to be coupled together when the second catheter is slidably disposed within the lumen of the first catheter such that a rotational orientation of the second catheter is fixed relative to a rotational orientation of the first catheter. The first proximal end portion can be a fitting, and the first key joint component can include an opening defined by the fitting.

10 Claims, 24 Drawing Sheets

(56) References Cited

U.S. PATENT DOCUMENTS

| | | | |
|---|---|---|---|
| 4,502,482 A | 3/1985 | DeLuccia | |
| 4,512,765 A | 4/1985 | Muto | |
| 4,716,896 A | 1/1988 | Ackerman | |
| 4,840,172 A | 6/1989 | Augustine et al. | |
| 5,135,490 A | 8/1992 | Strickland | |
| 5,246,012 A | 9/1993 | Strickland | |
| 6,053,166 A | 4/2000 | Gomez | |
| 6,064,902 A * | 5/2000 | Haissaguerre et al. | 600/381 |
| 6,306,097 B1 * | 10/2001 | Park et al. | 600/466 |
| 6,513,527 B1 | 2/2003 | Abdel-Aziz | |
| 6,568,393 B2 | 5/2003 | Christopher | |
| 2005/0103332 A1 | 5/2005 | Gingles et al. | |
| 2009/0292209 A1 * | 11/2009 | Hadjicostis | 600/463 |
| 2010/0300449 A1 | 12/2010 | Chan et al. | |

OTHER PUBLICATIONS

Airwaycam.com, Tracheal Tube Design and Delivery, http://www.airwaycam.com/intubation-Endotracheal-Tube-design.html, Copyright 2011, last accessed Jun. 24, 2011, 2 pages.

M. K. Sykes, Improved Plastic Endotracheal Tubes, British Medical Journal, Apr. 20, 1968, 1 page.

Co-pending U.S. Appl. No. 13/083,464, to Roberts et al., filed Apr. 8, 2011.

* cited by examiner

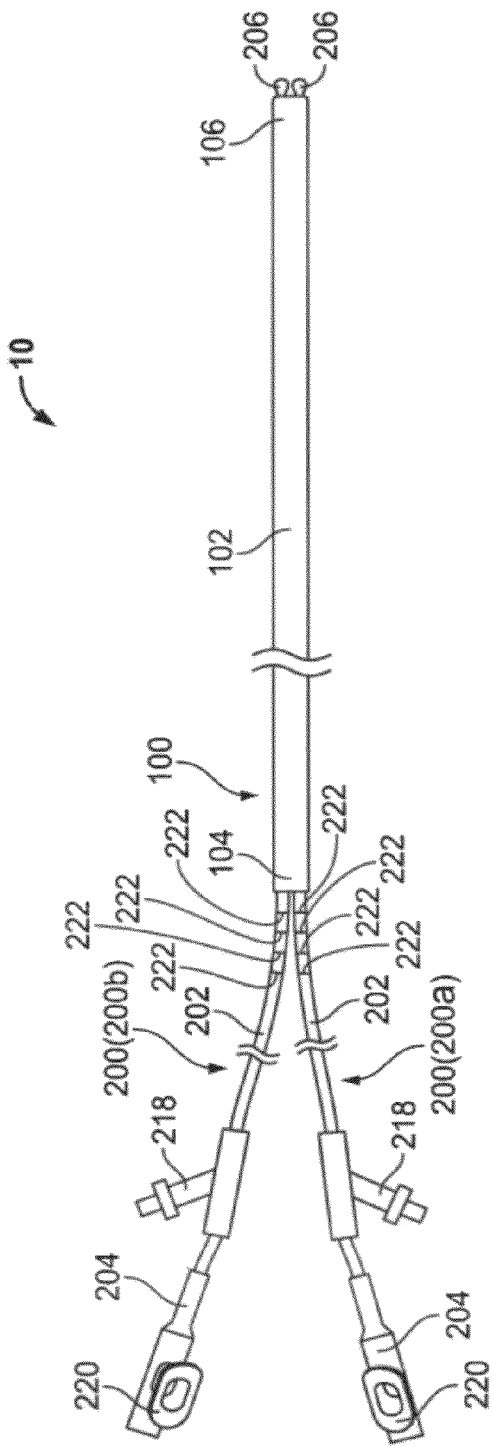
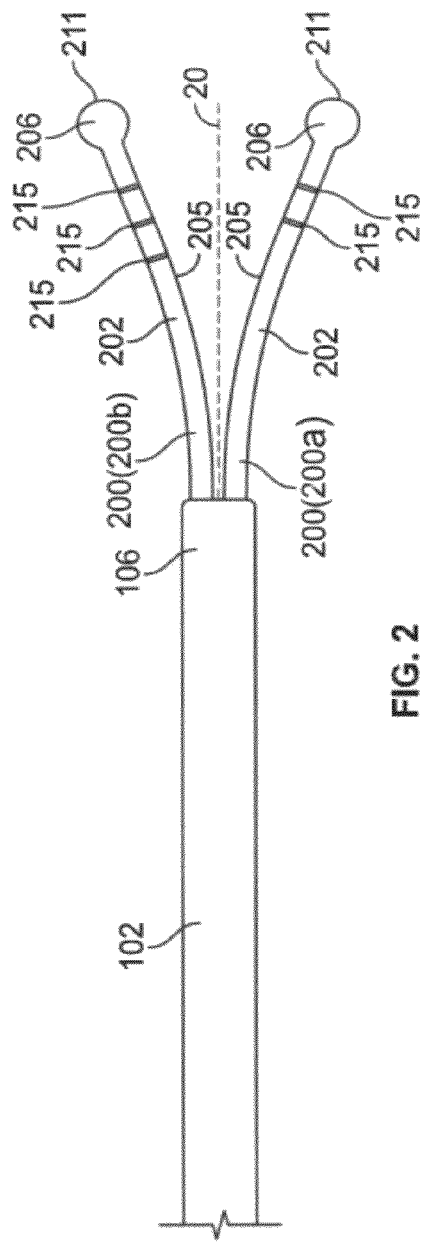

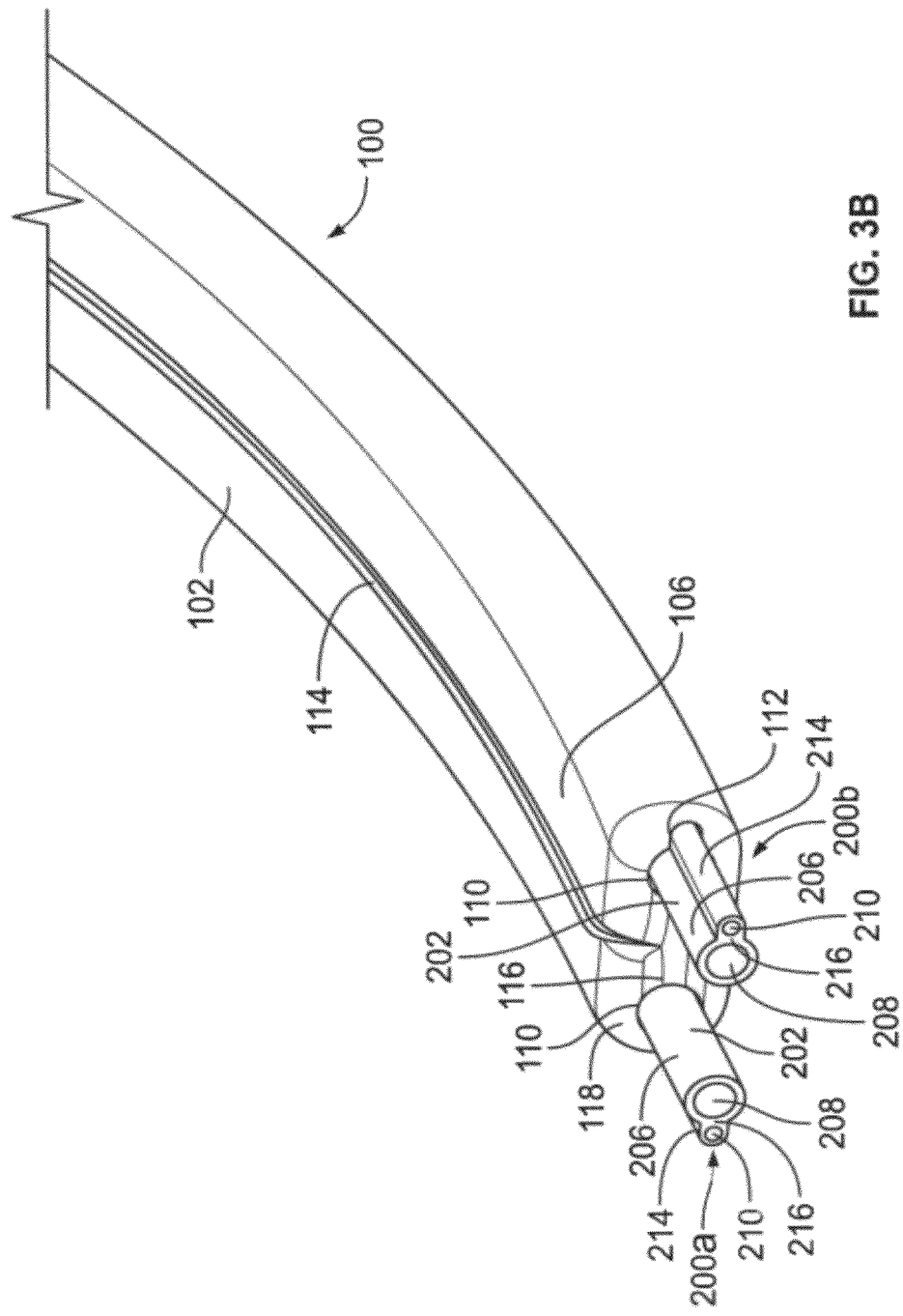

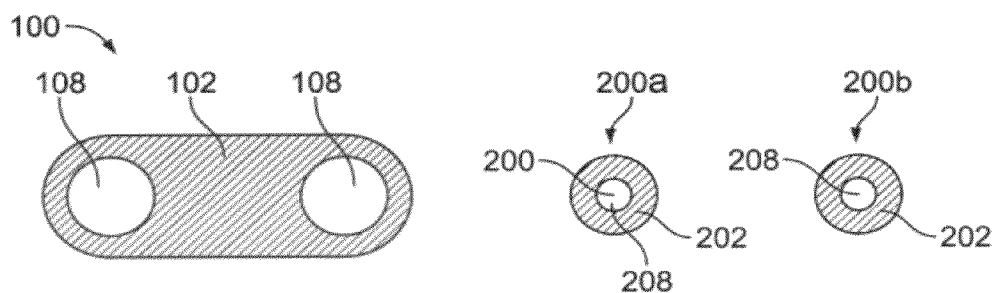
FIG. 4A
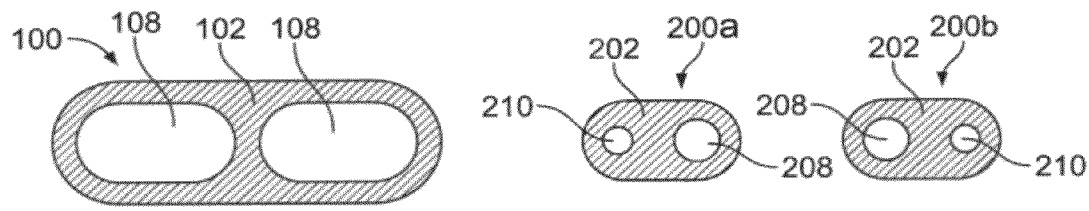
FIG. 4B
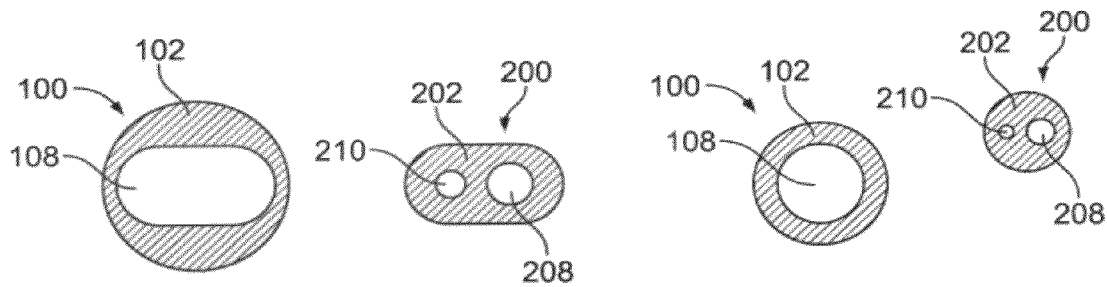
FIG. 4C  FIG. 4D
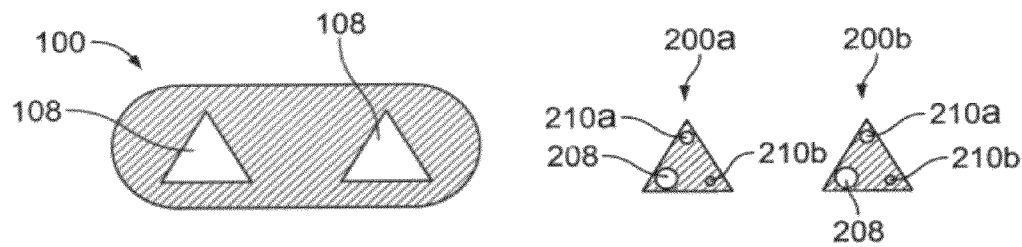
FIG. 4E

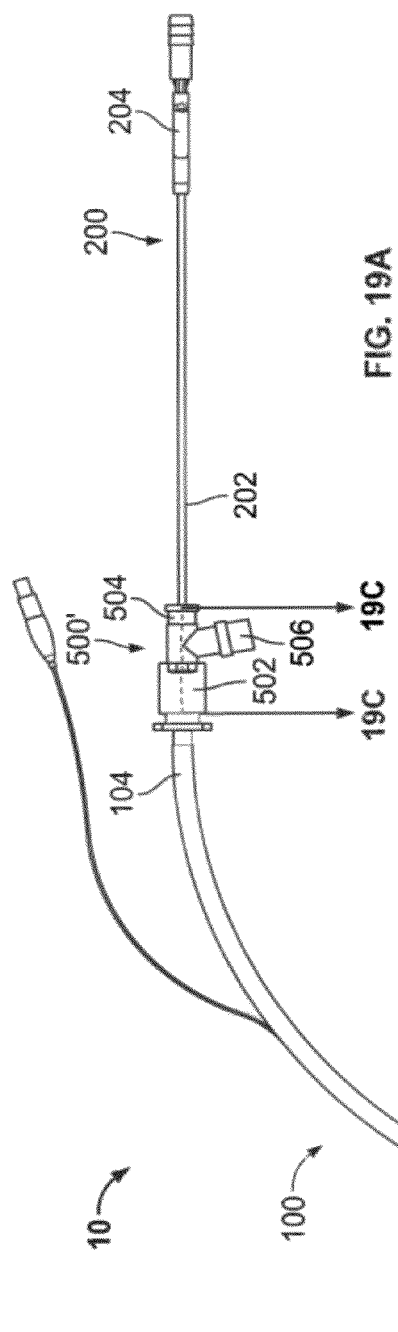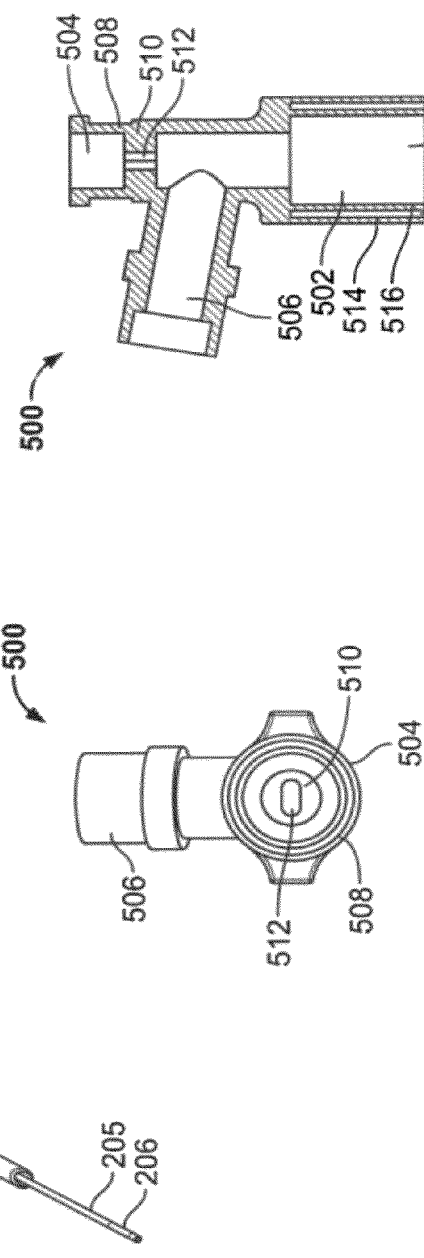

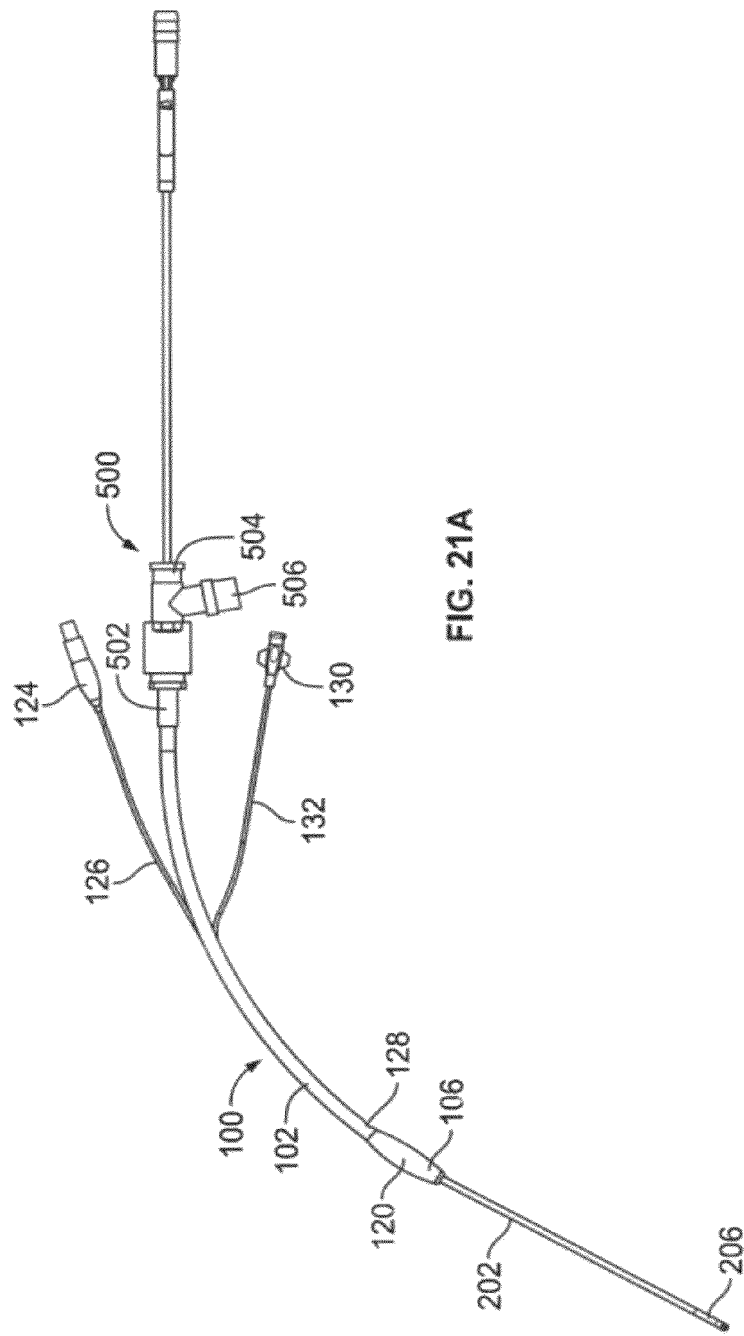
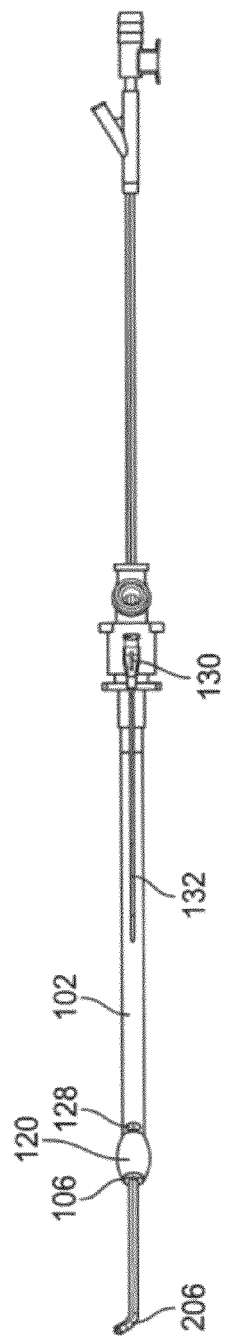
FIG. 21A
FIG. 21B

CATHETER SYSTEMS AND METHODS OF USE

CROSS-REFERENCE TO RELATED APPLICATION

This application is a continuation-in-part of U.S. patent application Ser. No. 13/083,462 to Roberts et al., filed Apr. 8, 2011, which shares a common disclosure with commonly owned, copending U.S. patent application Ser. No. 13/083,464 to Roberts et al., filed on Apr. 8, 2011, both of which are incorporated herein by reference in their entirety.

BACKGROUND

1. Field

The present invention relates to medical devices and, in particular, to catheters that can easily be advanced into tortuous body lumens and for which the location of the catheters within body lumens can easily be verified.

2. Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a target location.

One example of a tortuous pathway is the respiratory tract. The respiratory tract begins at the nose and mouth, which open to the trachea. The trachea travels downward into the chest at which it splits into the left and right main bronchi. The left and right main bronchi split at an angle from the trachea. The left main bronchus can be smaller in diameter than the right main bronchus and branches at a greater angle from the trachea than the angle at which the right main bronchus branches from the trachea. The main bronchi then split into lobar bronchi, which split into segmental bronchi. The segmental bronchi split into subsegmental bronchi.

Numerous procedures require intubation of the respiratory tract, including the left and right main bronchi, to aspirate mucus in the lungs or to delivery localized medicine, for example. Intubation of the left main bronchus from the trachea can be difficult because it may have a smaller diameter and greater angle relative to the trachea than the right main bronchus. For example, a typical procedure for aspirating fluid from the lungs can include introducing an endotracheal tube to the trachea of a patient, followed by extending a working catheter (e.g., an aspiration catheter) through a lumen of the endotracheal tube and into either the right or left main bronchus. Respiratory therapists seeking to intubate the left main bronchus with the aspiration catheter may mistakenly believe the left main bronchus has been intubated, when the catheter has actually entered the right main bronchus instead. In some instances, the endotracheal tube can be mistakenly inserted too deep so that its distal end extends into the right main bronchus, whereby the aspiration catheter can only access the right main bronchus. Often times, a specialist, such as a pulmonologist, is needed to insert a bronchoscope into the left main bronchus and aspirate the left main bronchus using the working channel of the bronchoscope. The bronchoscope is equipped with a vision system (including, for example, a fiberoptic system) and/or a fluoroscopic imaging system, to guide the bronchoscope into the left main bronchus. However, visualization equipment and the endoscopic procedure can be expensive, and specialists may not be readily available to conduct the procedure when desired.

BRIEF SUMMARY

What is needed is a catheter system having an outer delivery catheter and an inner working catheter (e.g., an aspiration catheter) that can easily intubate a chosen body lumen (e.g., the left main bronchus), without requiring an endoscopic procedure to ensure that the working catheter has actually entered the chosen body lumen (e.g., the left main bronchus), and not another lumen (e.g., the right main bronchus). Also what is needed is a catheter system in which the desired placement of a working catheter within a chosen body lumen can be easily verified without using endoscopy to assure placement.

A catheter system can include a first catheter and a second catheter. The first catheter includes a first proximal end portion, a first elongated body portion, a first distal end portion, and a lumen extending through the first elongated body portion from the first proximal end portion to the first distal end portion. The first proximal end portion has a first key joint component that extends along a partial length of the first proximal end portion. The second catheter includes a second elongated body portion, a second distal end portion, and a second key joint component that corresponds with the first key joint component. The first key joint component and the second key joint component are configured to be coupled together when the second catheter is slidably disposed within the lumen of the first catheter such that a rotational orientation of the second catheter is fixed relative to a rotational orientation of the first catheter.

A catheter fitting can include a first portion and a second portion. The first portion is configured to selectively couple to a first catheter. The second portion defines a first opening configured to receive a second catheter. The first opening has a non-circular shape that corresponds to a non-circular outer contour of the second catheter.

A kit can include a first catheter and a fitting. The first catheter includes an elongated body portion and a distal end portion. The distal end portion has a pre-formed bend that extends at a non-zero angle relative to a longitudinal axis of a first body lumen. The first catheter has a non-circular outer contour. The fitting includes a first portion and a second portion. The first portion of the fitting is configured to selectively couple to a second catheter. The second portion of the fitting defines a first opening configured to receive the first catheter such that a rotational orientation of the first catheter is fixed relative to a rotational orientation of the second catheter. The first opening has a non-circular shape that corresponds to the non-circular outer contour of the first catheter.

A catheter can include an elongated body having a proximal end portion, a distal end portion, and a lumen extending from the proximal end portion to the distal end portion. The distal end portion of the catheter includes a pre-formed bend that extends at a non-zero angle relative to a longitudinal axis of a body lumen. The catheter can also include an antenna having a distal portion disposed on the distal end portion of the elongated body configured for emitting a signal that can be detected outside a body.

Methods for using catheters catheter systems according to embodiments described herein are also provided.

BRIEF DESCRIPTION OF THE DRAWINGS/FIGURES

Embodiments of the present invention are described with reference to the accompanying drawings. In the drawings, like reference numbers indicate identical or functionally similar elements.

FIG. 1 illustrates a plan view of a catheter system including an outer catheter and two inner catheters according to an embodiment presented herein.

FIG. 2 illustrates a plan view of the catheter system of FIG. 1 according to an embodiment presented herein.

Figure 3A:
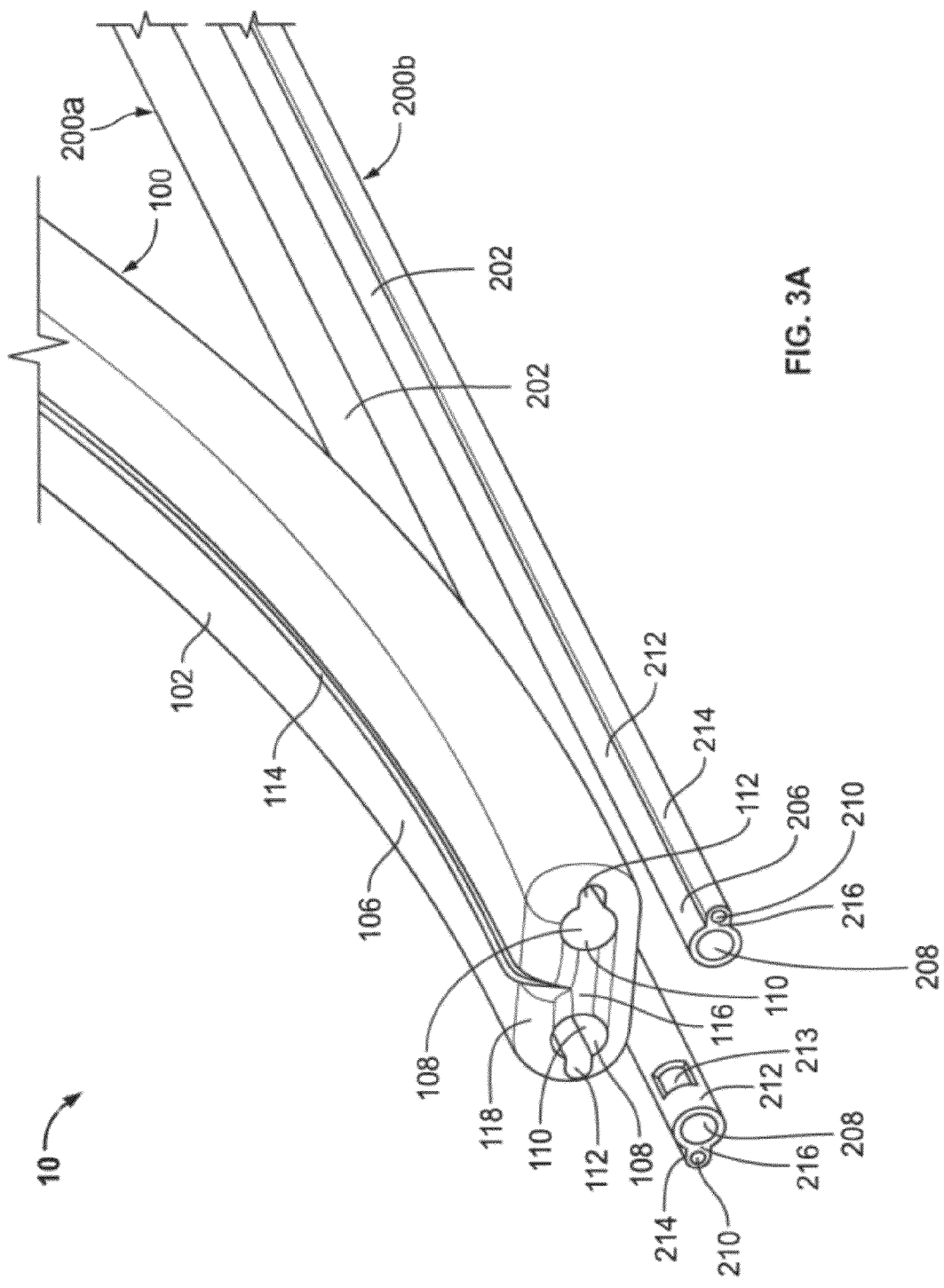

FIG. 3A schematically illustrates an exploded, distal perspective view of the catheter system of FIG. 1 showing key joint components of the outer catheter and inner catheters according to an embodiment presented herein.

FIG. 3B schematically illustrates the catheter system of FIG. 3A showing the inner catheters disposed in the outer catheter according to an embodiment presented herein.

FIGS. 4A-4E illustrate cross-sectional views of exemplary catheter and lumen configurations for an outer catheter and inner catheter(s) according to embodiments presented herein.

Figure 5:
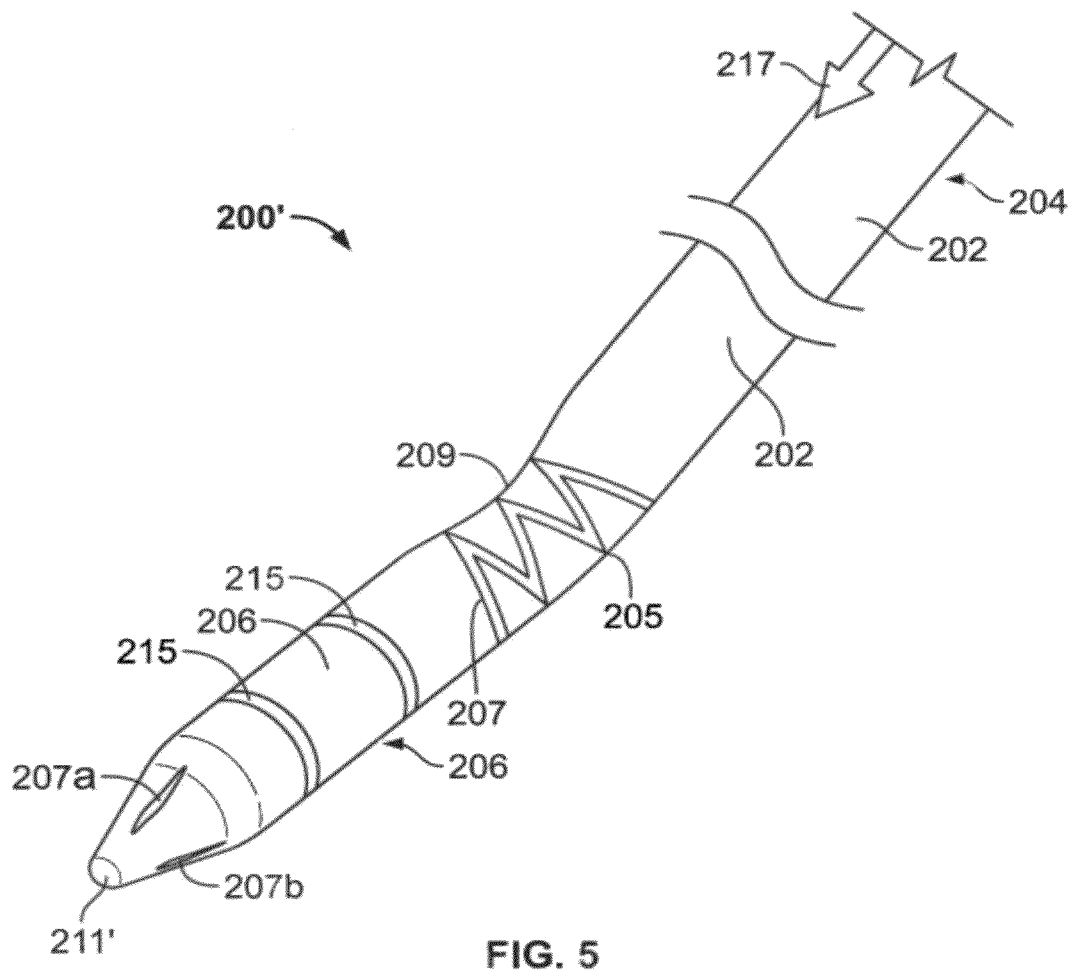

FIG. 5 illustrates a perspective view of an inner catheter having a conical shaped distal end according to an embodiment presented herein.

Figure 6A:
Figure 6B:
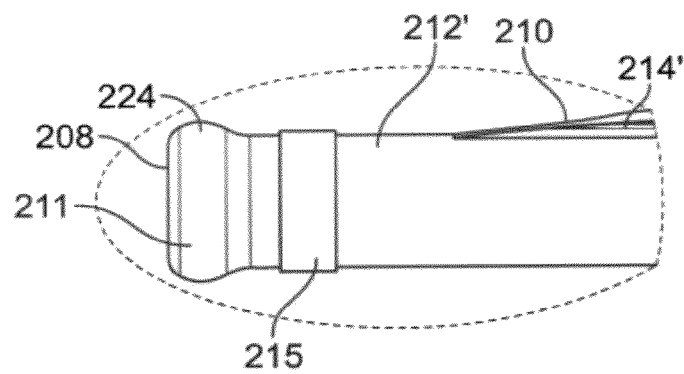
Figure 6C:
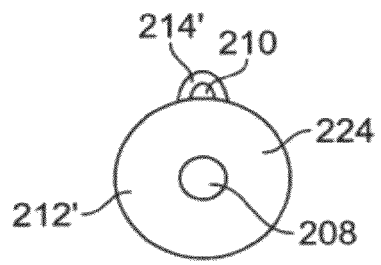

FIGS. 6A, 6B, and 6C illustrate a side view, an enlarged side view, and a front view, respectively, of an inner catheter according to an embodiment presented herein.

Figure 7:
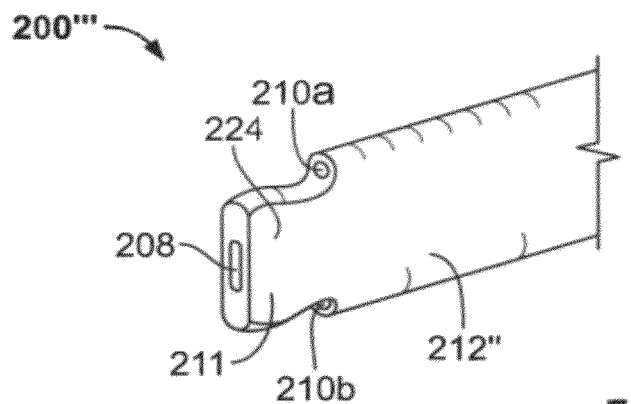

FIG. 7 illustrates a perspective side view of a distal end portion of an inner catheter according to an embodiment presented herein.

Figure 8A:
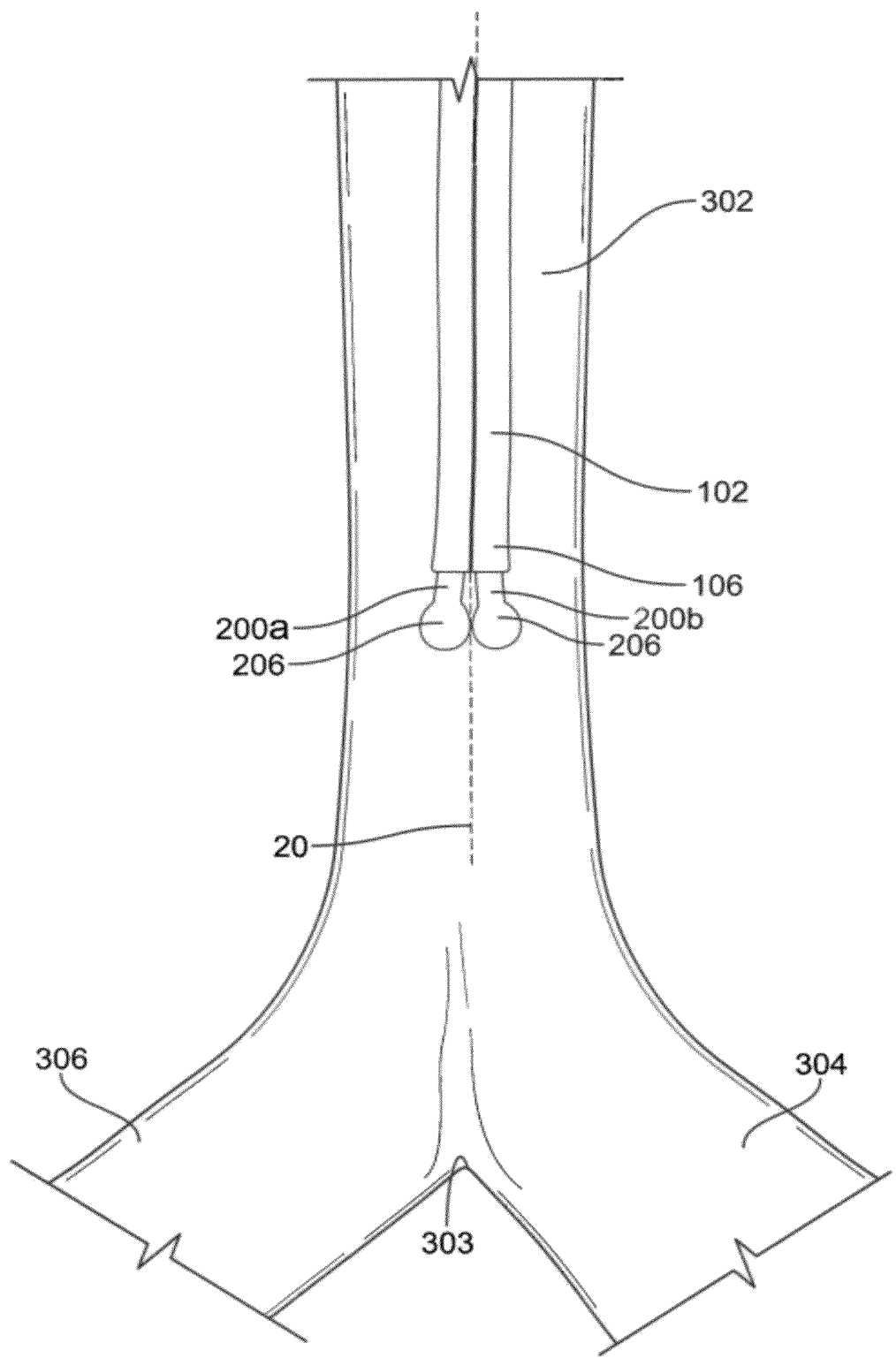

FIG. 8A illustrates the catheter system of FIG. 1 positioned within a trachea according to an embodiment presented herein.

Figure 8B:
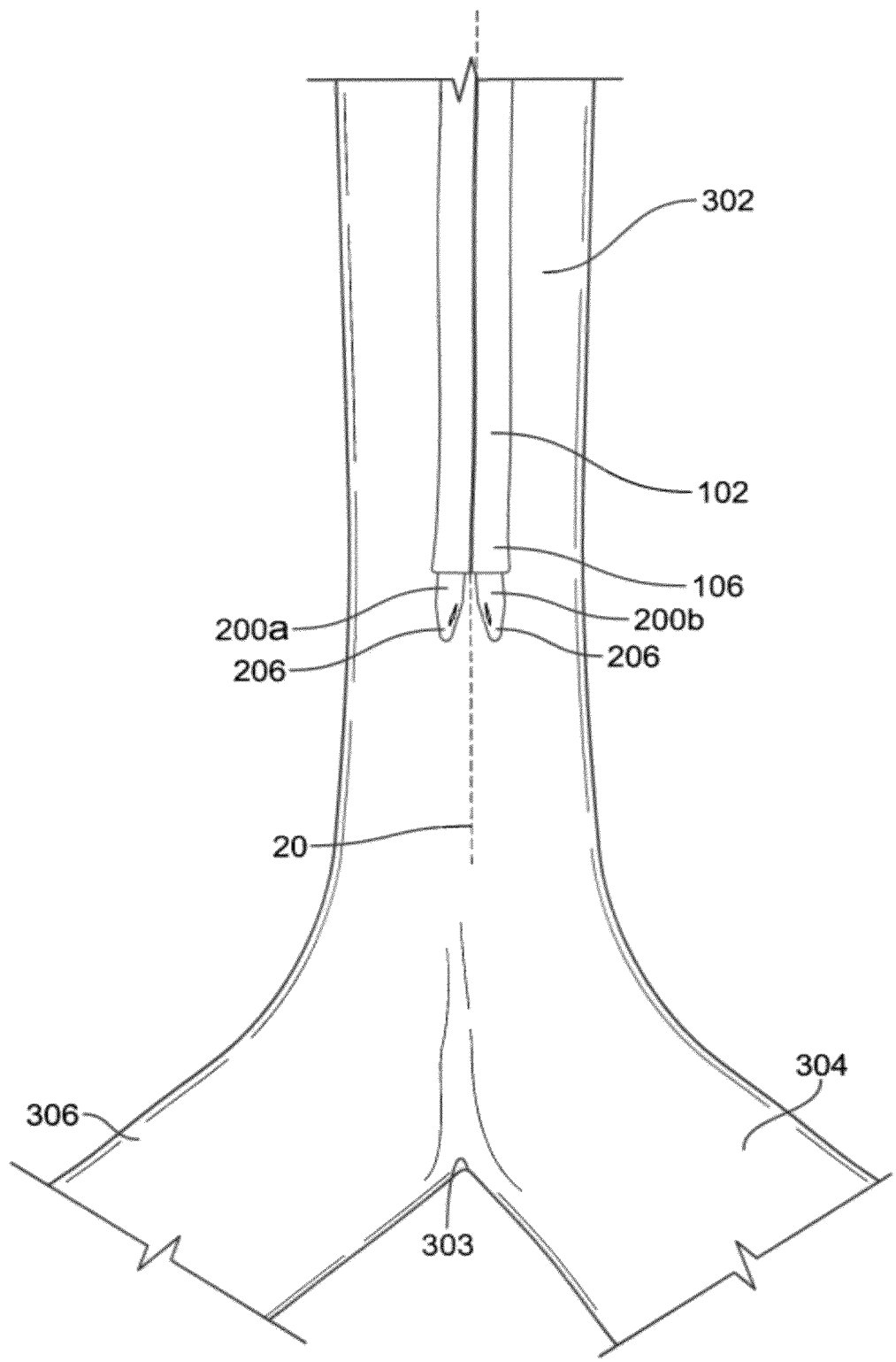

FIG. 8B illustrates the catheter system of FIG. 1 with inner catheters of FIG. 5 within a trachea according to an embodiment presented herein.

Figure 9:
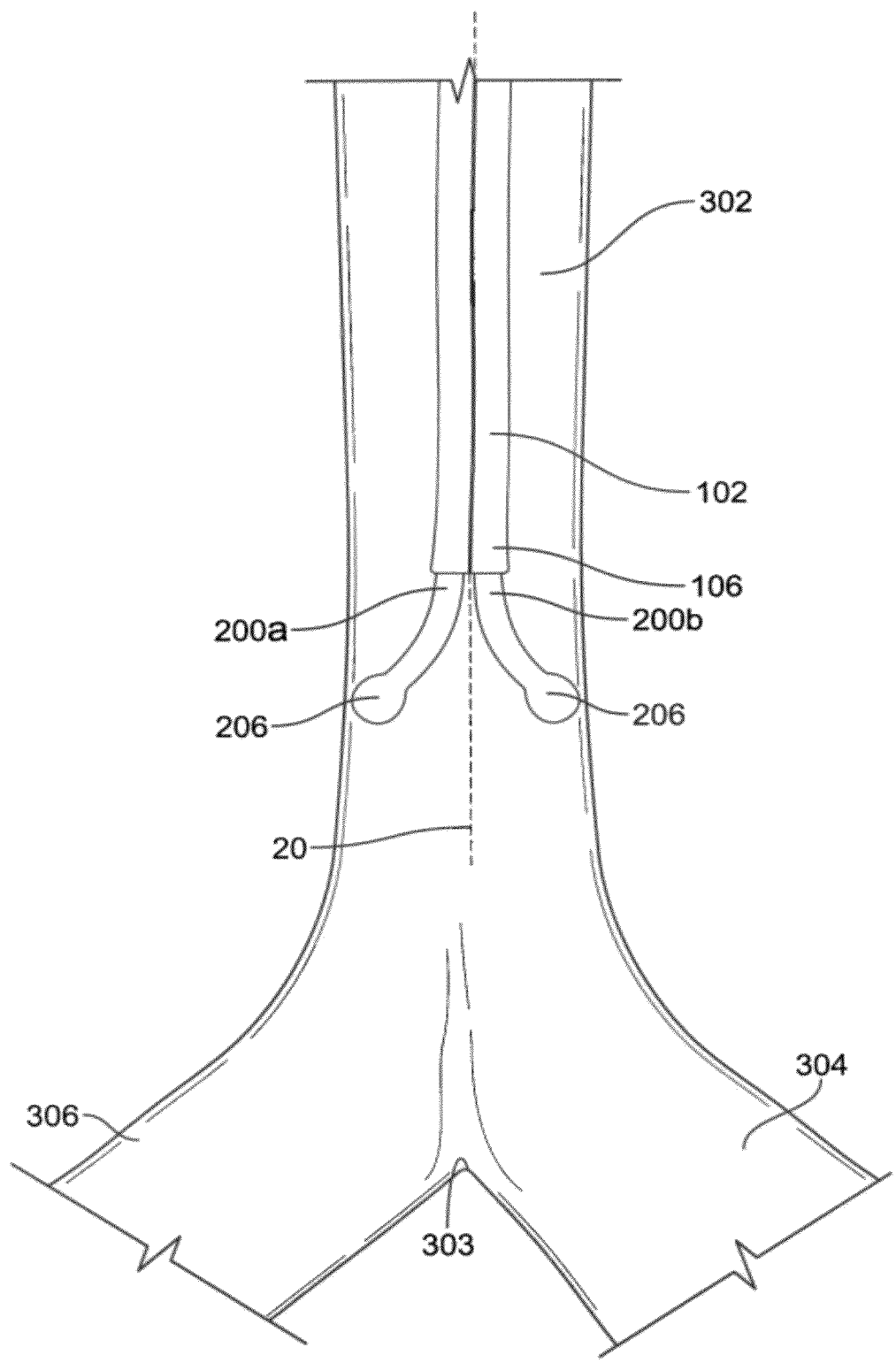

FIG. 9 illustrates the catheter system of FIG. 1 in which the distal end portions of the two inner catheters are extended from the distal end of the outer catheter according to an embodiment presented herein.

Figure 10:
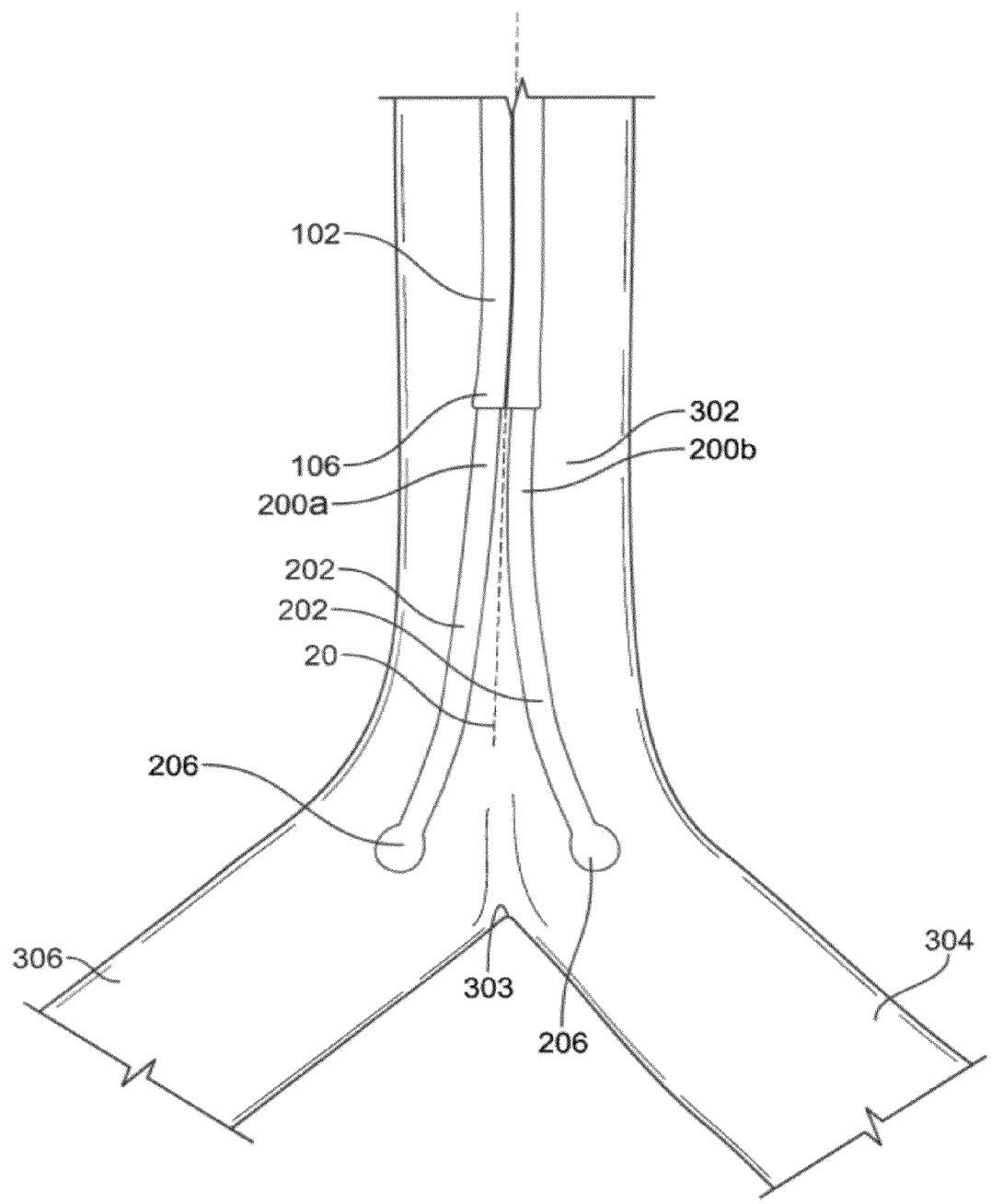

FIG. 10 illustrates the catheter system of FIG. 1 in which the distal end portions of the two inner catheters are extended from the distal end of the outer catheter according to an embodiment presented herein.

Figure 11:
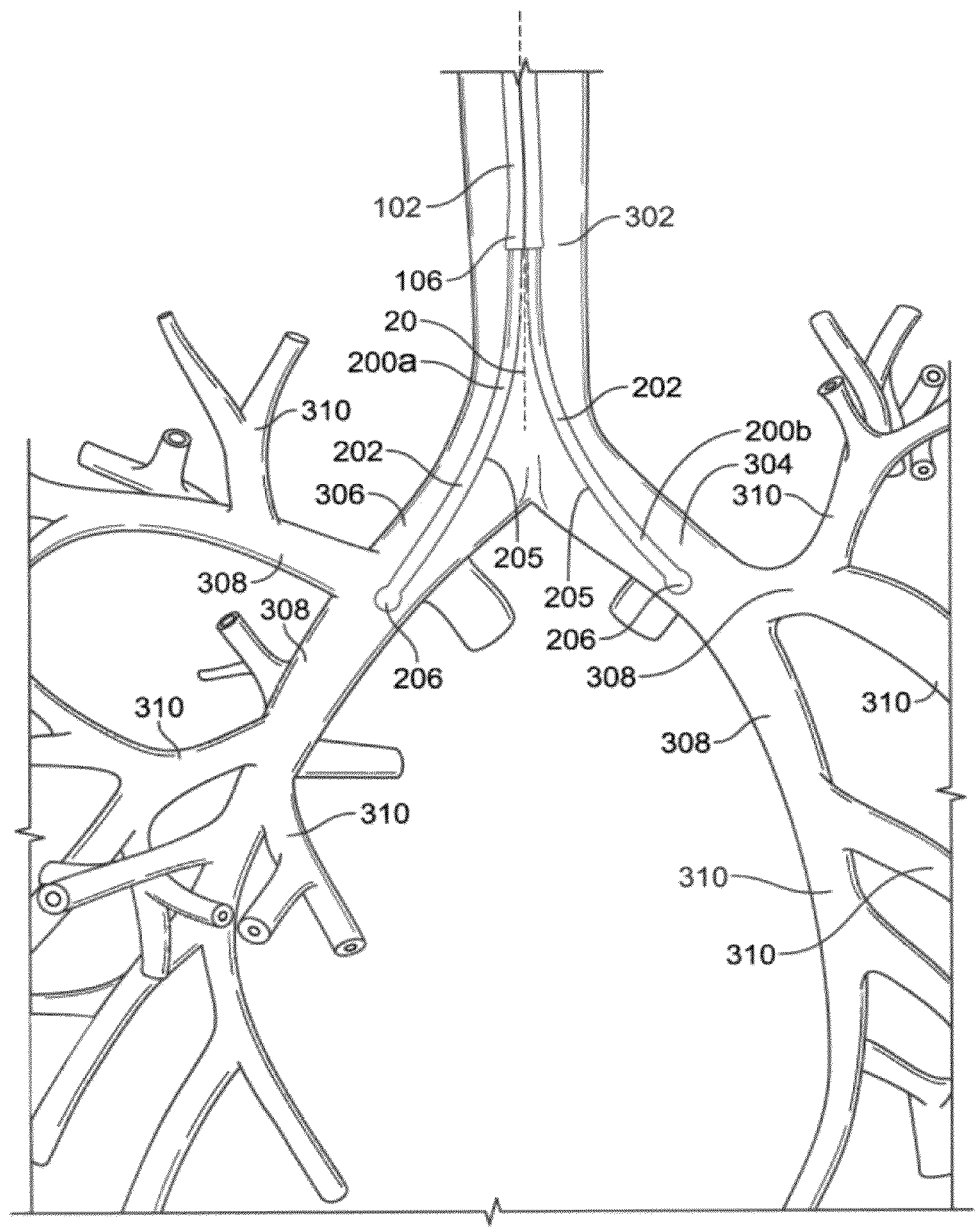

FIG. 11 illustrates the catheter system of FIG. 1 in which the distal end portions of the two inner catheters extend into left and right main bronchi according to an embodiment presented herein.

Figure 12:
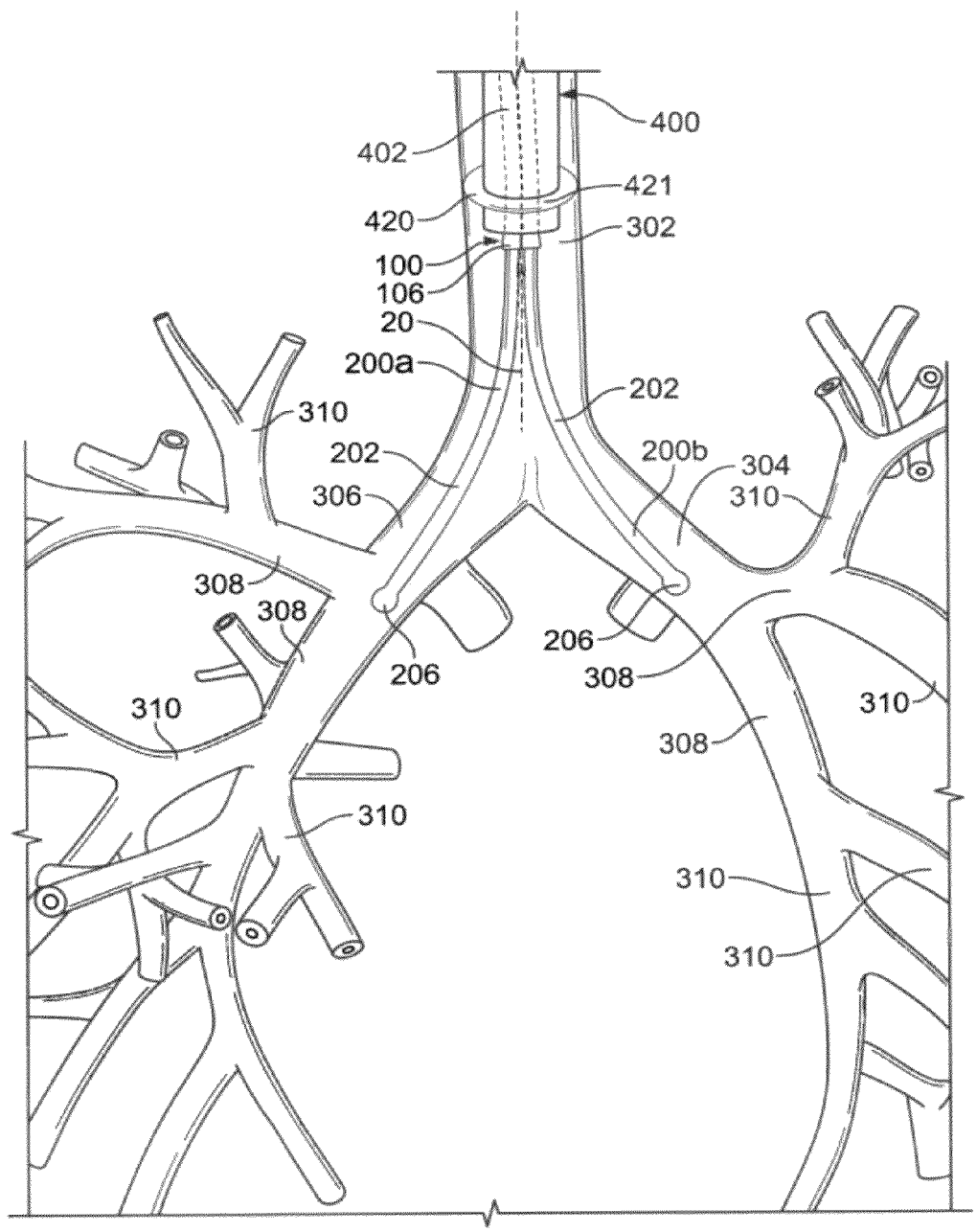

FIG. 12 illustrates the catheter system of FIG. 1 inserted through a third catheter having an expandable support member securing the third catheter in position in the trachea according to an embodiment presented herein.

Figure 13:
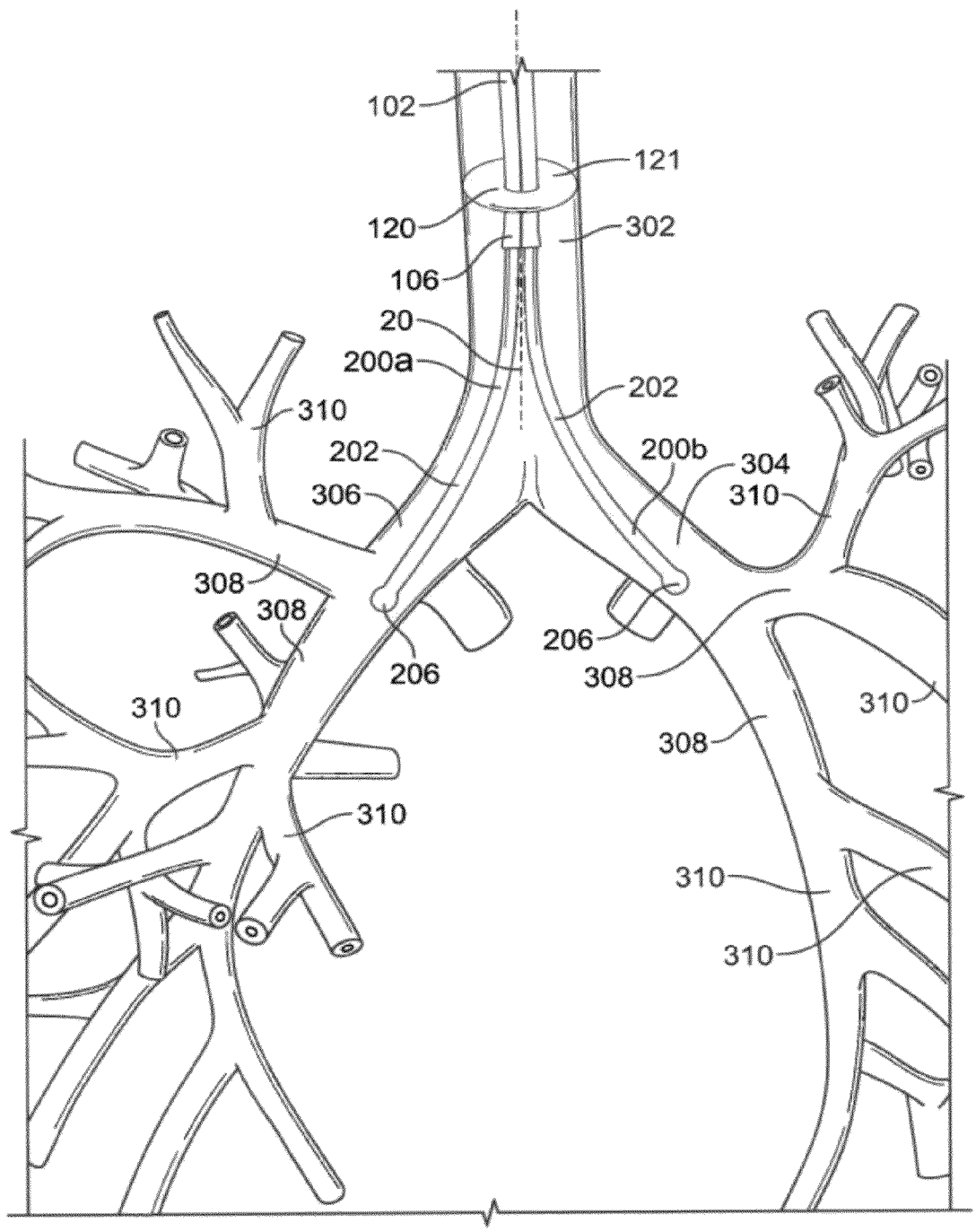

FIG. 13 illustrates the catheter system of FIG. 1 having an expandable support member securing the outer catheter in position in the trachea according to an embodiment presented herein.

Figure 14:
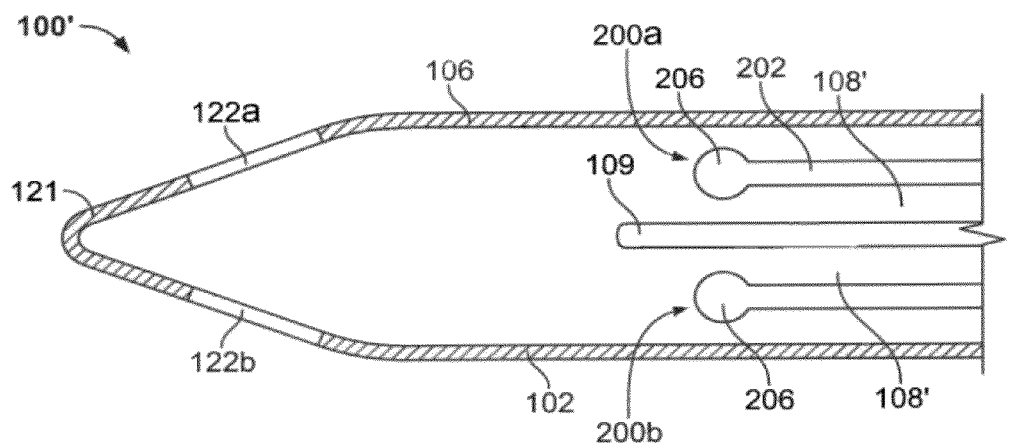

FIG. 14 illustrates a cross-sectional view of a catheter system according to an embodiment presented herein.

Figure 15:
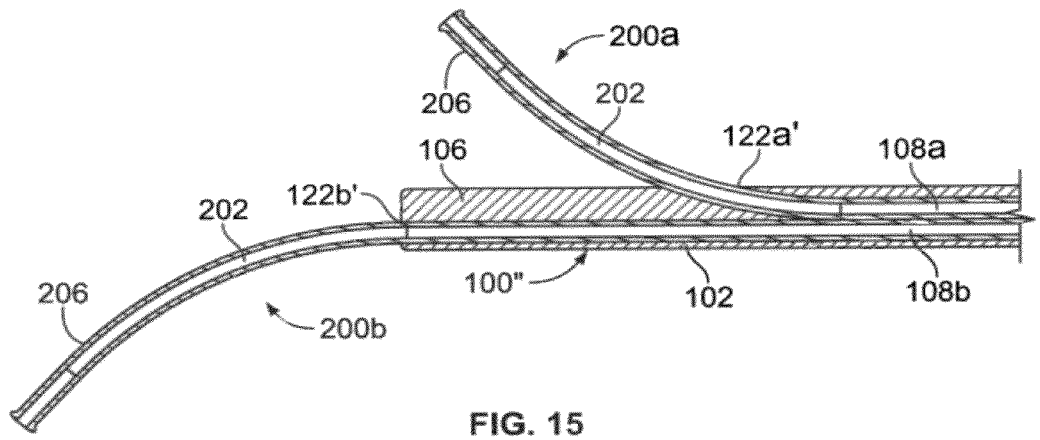

FIG. 15 illustrates a cross-sectional view of a catheter system according to an embodiment presented herein.

Figure 16:
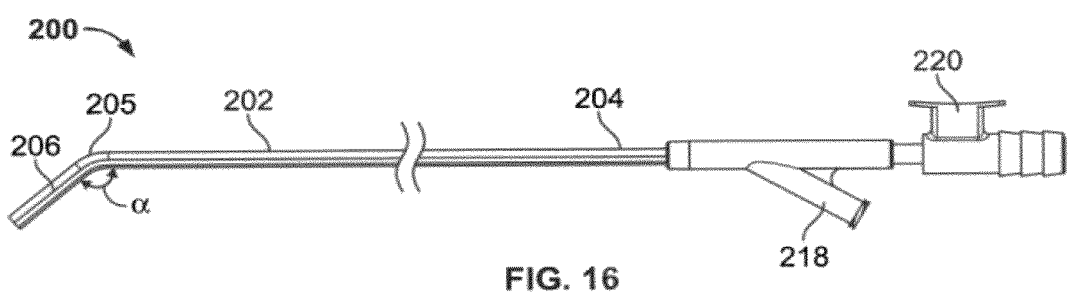

FIG. 16 illustrates a side view of an inner catheter according to an embodiment presented herein.

Figures 17, 18:
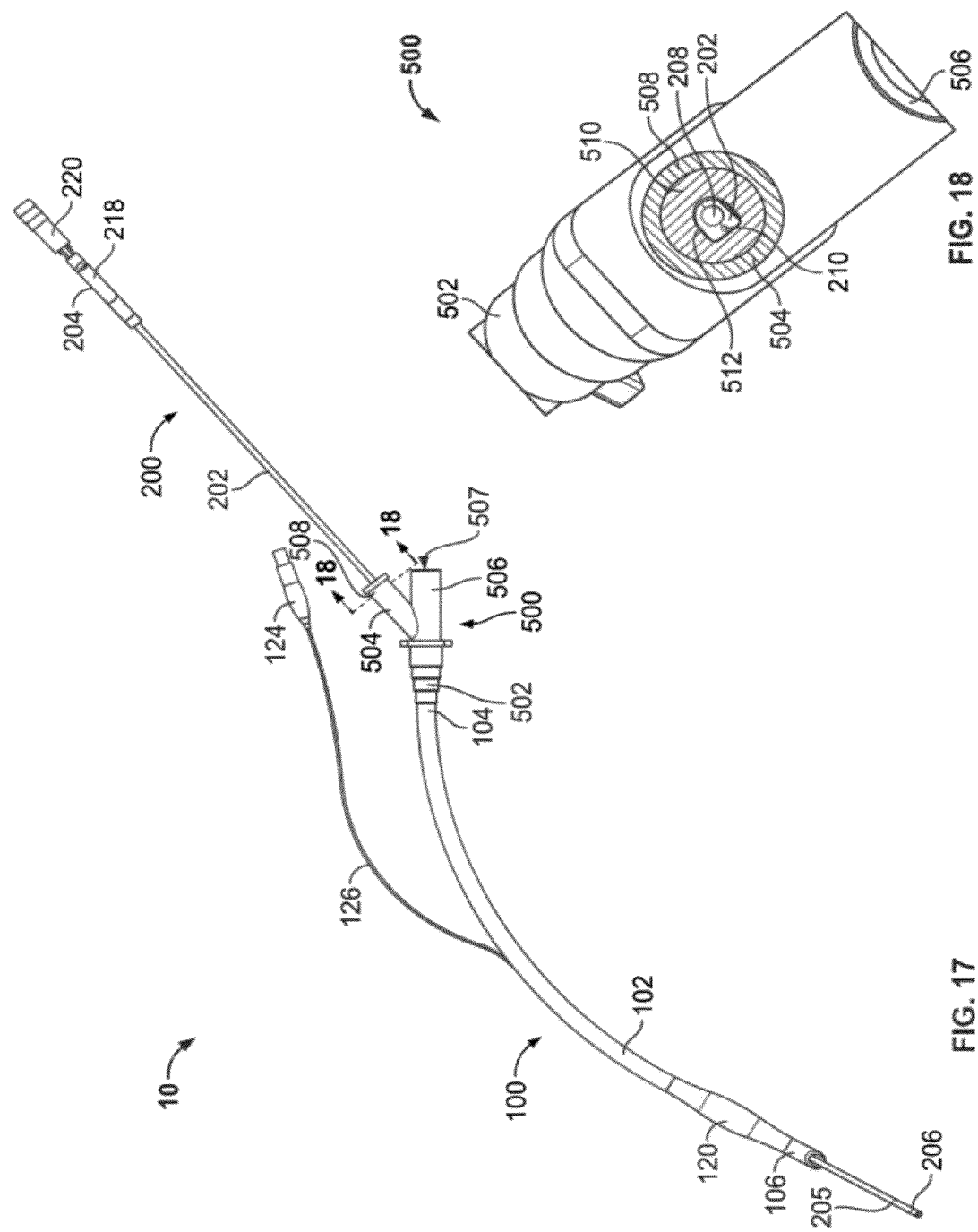

FIG. 17 illustrates a side view of a catheter system including a fitting according to an embodiment presented herein.

FIG. 18 illustrates a cross-sectional view of the catheter system of FIG. 17 according to an embodiment presented herein.

FIG. 19A illustrates a side view of a catheter system including a fitting according to an embodiment presented herein.

FIGS. 19B and 19C illustrate a back view and cross-sectional view, respectively, of the fitting of FIG. 19A according to an embodiment presented herein.

Figure 20A:
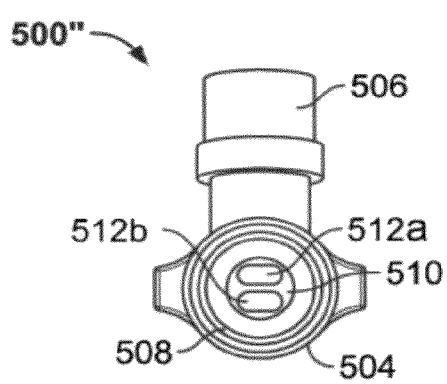
Figure 20B:
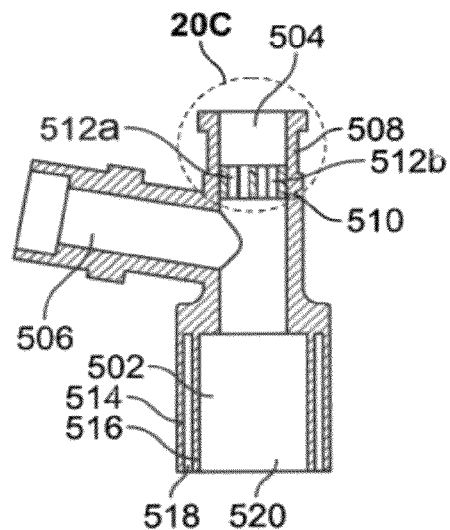
Figure 20C:
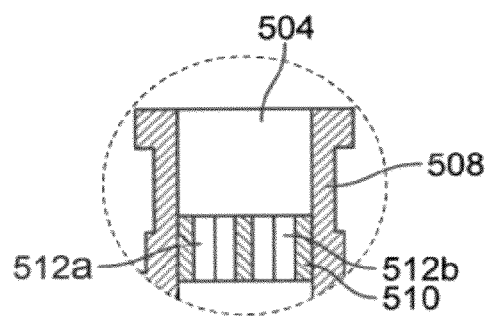

FIGS. 20A and 20B illustrate a back view and cross-sectional view of a fitting of according to an embodiment presented herein. FIG. 20C illustrates a cross-sectional view of a fitting according to an embodiment presented herein.

FIGS. 21A and 21B illustrate a side view and a top view, respectively, of a catheter system including a fitting according to an embodiment presented herein.

Figure 22:
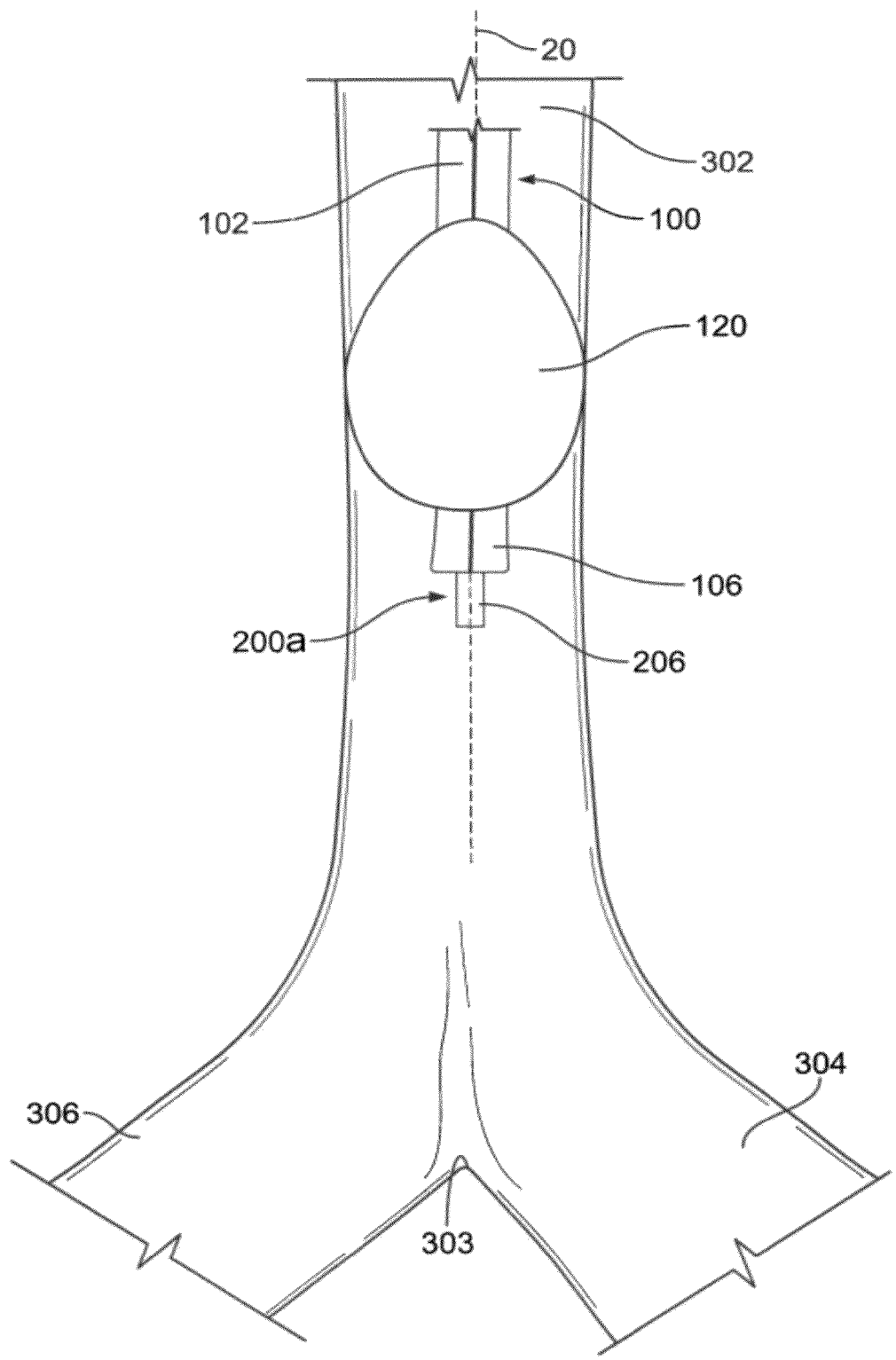

FIG. 22 illustrates the catheter system of FIG. 17 positioned within a trachea according to an embodiment presented herein.

Figure 23:
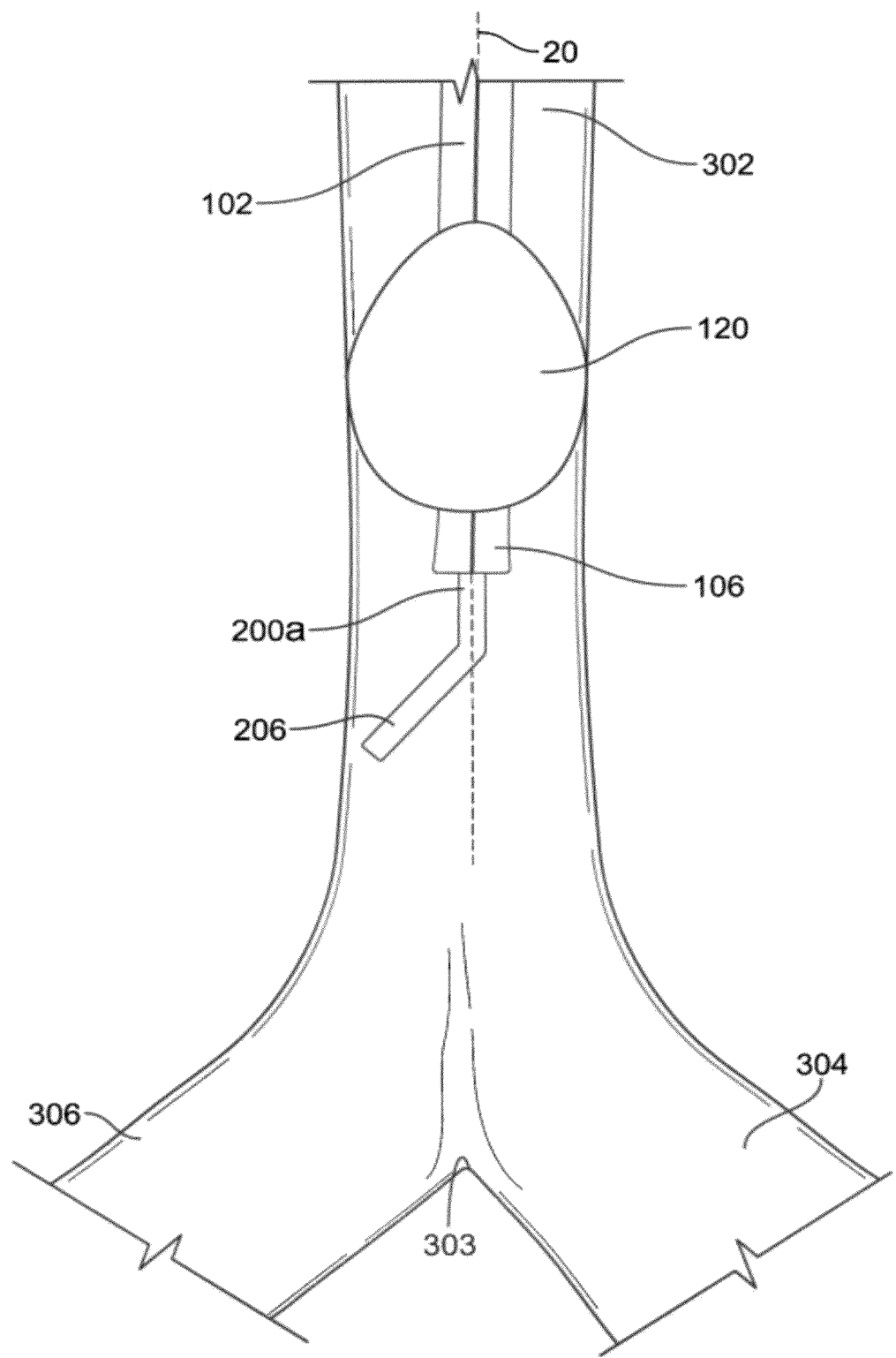

FIG. 23 illustrates the catheter system of FIG. 17 in which the distal end portion of the inner catheter is extended from the distal end of the outer catheter according to an embodiment presented herein.

Figure 24:
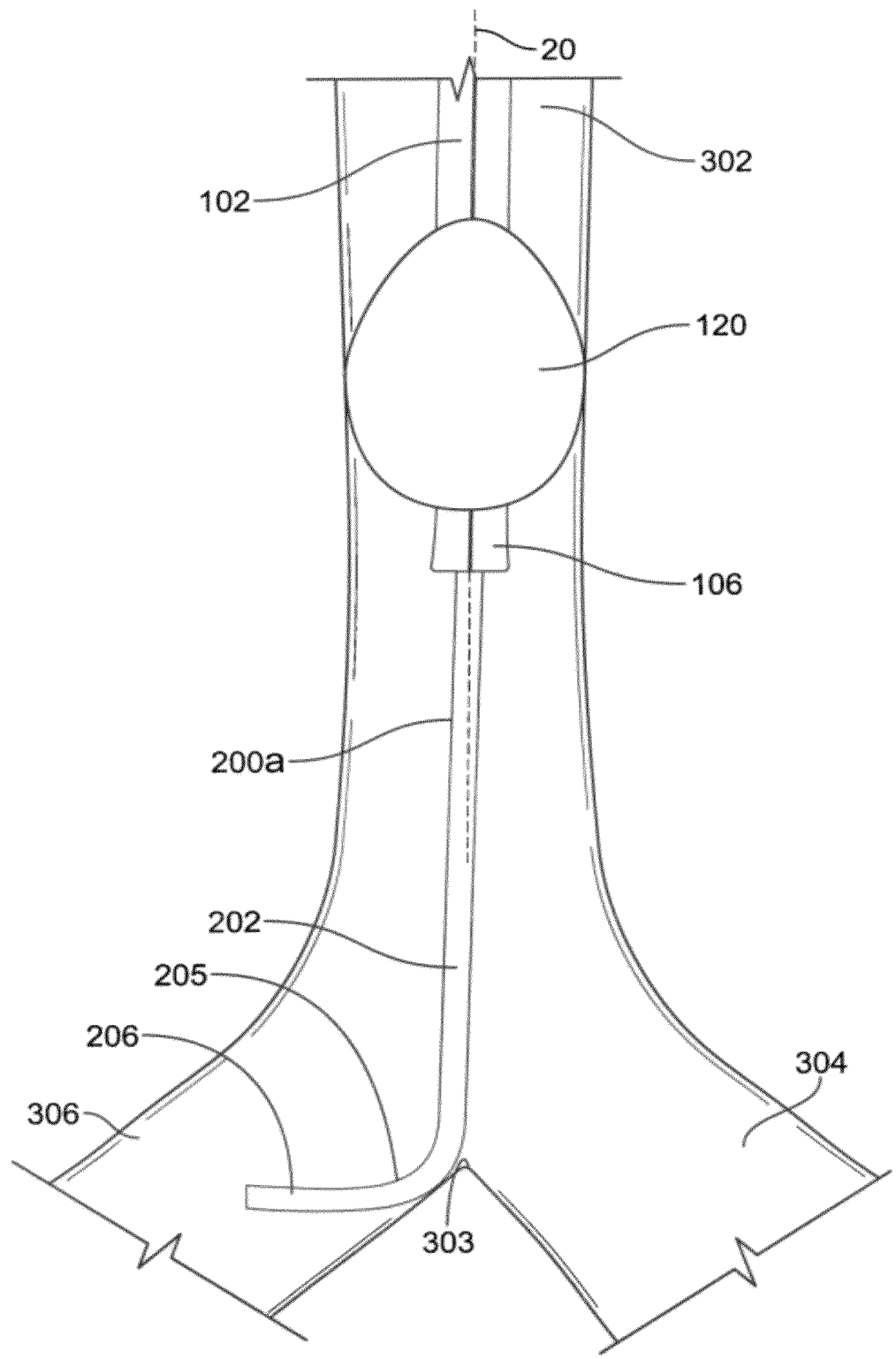

FIG. 24 illustrates the catheter system of FIG. 17 in which the distal end portion is extended into the right main bronchus according to an embodiment presented herein.

Figure 25:
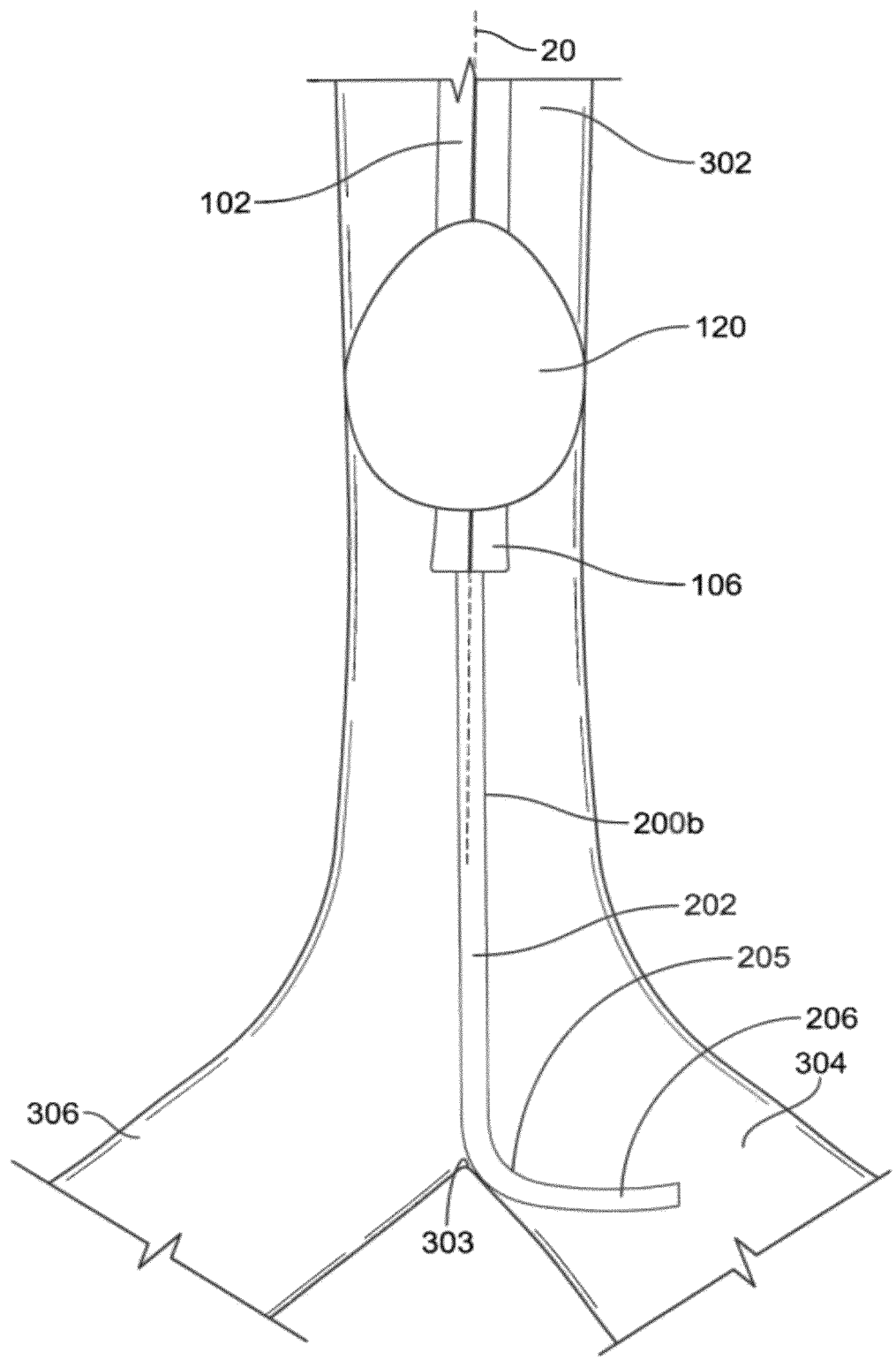

FIG. 25 illustrates the catheter system of FIG. 17 in which the distal end portion is extended into the left main bronchus according to an embodiment presented herein.

Figure 26:
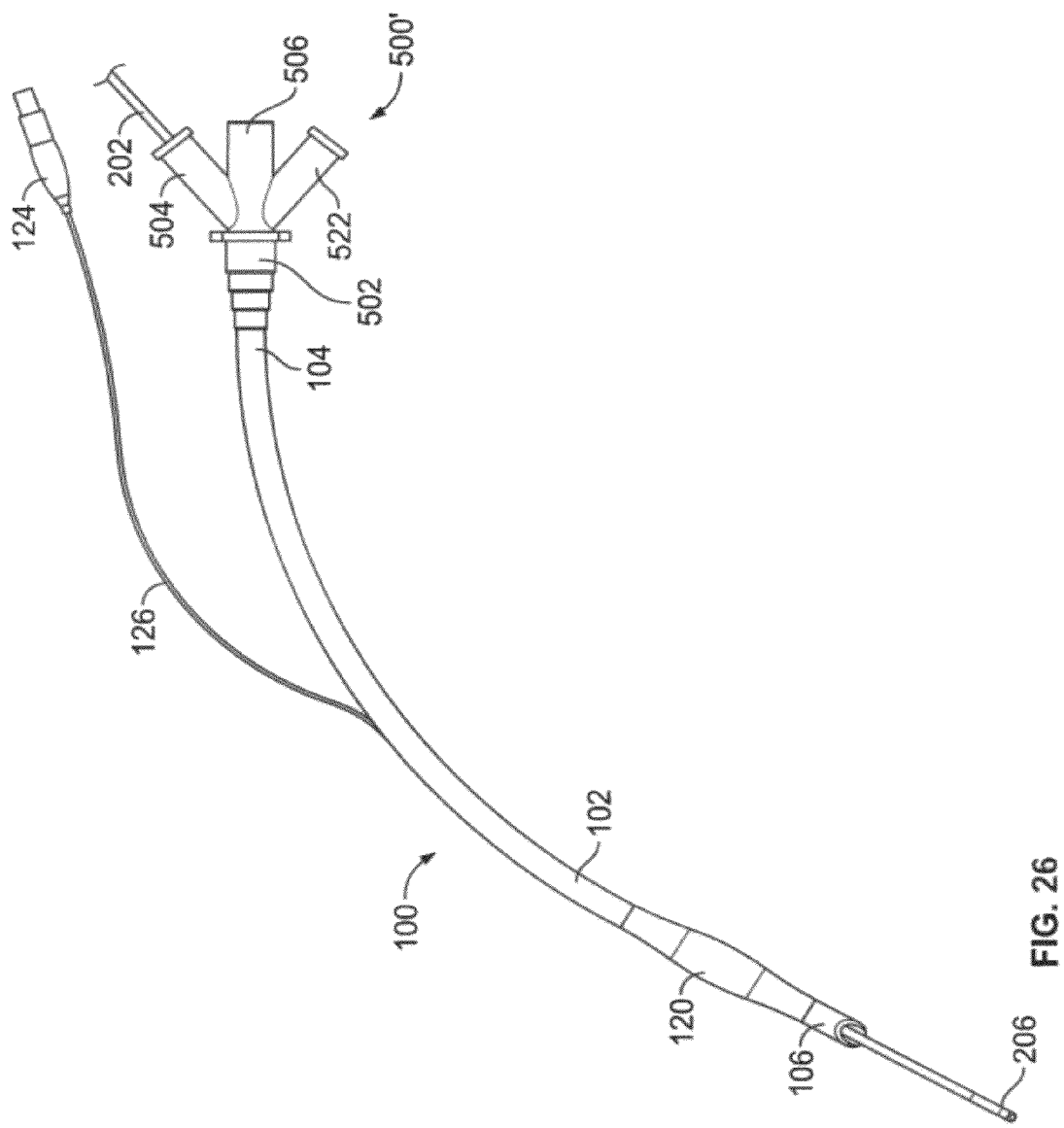

FIG. 26 illustrates a catheter system including a fitting according to an embodiment presented herein.

Figure 27A:
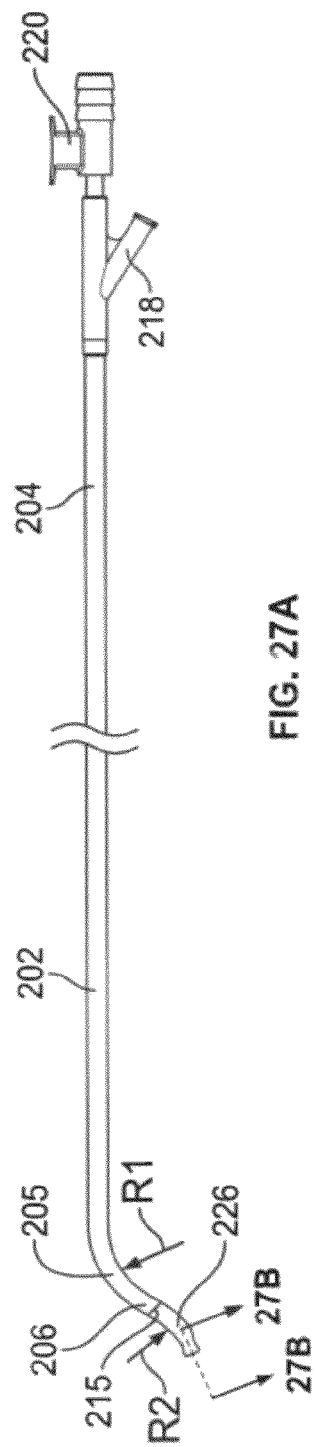
Figure 27B:
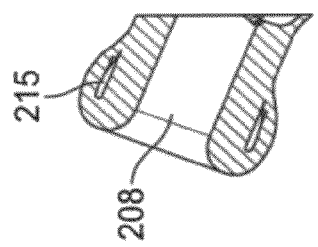

FIGS. 27A and 27B illustrate a side view and a cross-sectional view of a catheter having a compound bend according to an embodiment presented herein.

The features and advantages of the present invention will become more apparent from the detailed description set forth below when taken in conjunction with the drawings, in which like reference characters identify corresponding elements throughout.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such a feature, structure, or characteristic in connection with other embodiments whether or not explicitly described.

FIGS. 1, 2, 3A, and 3B illustrate a catheter system 10 according to some embodiments. Catheter system 10 can include an outer catheter 100 which slidably receives therein one or more inner catheter(s) 200. In the embodiments shown in the Figures, catheter system 10 includes two inner catheters 200a and 200b. However, it should be understood that the embodiments of catheter system 10 illustrated in the Figures are shown as non-limiting examples only. Thus, in some embodiments, catheter system 10 can be configured to have only one inner catheter 200, or in some embodiments can be configured to have more than two inner catheters without departing from the general concept of the present invention.

Outer catheter 100 can include an elongated body 102 having a proximal end portion 104 and a distal end portion 106. Elongated body 102 can have a longitudinal axis 20 as illustrated in FIG. 2. Outer catheter 100 can be configured to be inserted in to a body lumen. Elongated body 102 can have a length such that when distal end portion 106 is at a desired target location within a body lumen, proximal end portion 104 is outside the body. For example, outer catheter 100 can be an endotracheal tube having a distal end portion 106 inserted into a trachea through an incision in the throat or through the mouth or nose, and a proximal end portion 104 outside the body.

Elongated body 102 can define one or more lumen(s) 108 extending from proximal end portion 104 to distal end portion 106. Lumen(s) 108 can have openings at proximal end portion 104 and at distal end portion 106. Lumen(s) 108 can slidably receive one or more catheters 200 through the opening at proximal end portion 104. In some embodiments, elongated body 102 can define one lumen 108 configured to slidably receive one or more inner catheters 200. For example, in some embodiments, the one lumen can receive one inner catheter 200, and in some embodiments, the one lumen can receive two inner catheters 200 (such as inner catheters 200a and 200b, as shown in FIGS. 1 and 2). In some embodiments, as shown in FIGS. 3A and 3B, elongated body 102 can define two lumens 108 separated from each other by an intermediate wall portion 116 that can extend the length of elongated body 102. The two lumens 108 are configured to receive one of respective catheters 200a and 200b. Lumen(s) 108 can also include a key joint component that corresponds to a key joint component on inner catheter 200 to fix the rotational orientation of inner catheter relative to outer catheter 100 as later described with reference to FIGS. 3A and 3B. In some embodiments, the outer contour of elongated body 102 can be circular, oval, or any other suitable shape. In some embodiments, the outer contour of elongated body 102 corresponds to the shape of the body lumen in which elongated body 102 passes.

Any of the embodiments of outer catheter 100 described herein can be an endotracheal tube, and in some embodiments, outer catheter 100 can have a Murphy eye (not shown) at distal end portion 206, as known to one skilled in the art. A method of proper placement of outer catheter 100 in a trachea as further described with reference to FIG. 13 can render a Murphy eye (even if provided) unnecessary. With proper placement of outer catheter 100, it can be ensured that distal end portion 106 of outer catheter 100 is spaced a sufficient distance away from the carina and trachea walls, which can obstruct airflow.

Inner catheter 200 can include an elongated body 202 having a proximal end portion 204 and a distal end portion 206. Elongated body 202 can define one or more lumens having an opening at proximal end portion 204 and an opening at distal end portion 206. For example, elongated body 202 can define a first lumen 208 and a second lumen 210 that extend from proximal end portion 204 to distal end portion 206. At proximal end portion 204, first lumen 208 can have a port 220, and second lumen 210 can have a port 218. FIG. 1 illustrates port 220 and port 218 of inner catheter 200 according to an embodiment. Port 220 can be configured to couple to a device that creates a suction for removing substances through first lumen 208. Port 218 can be configured to couple to a pump and/or a fluid supply for delivering fluid through second lumen 210. Ports 218 and 220 can be positioned on elongated body 202 such that they remain outside the body when distal end portion 206 is within a body lumen.

First lumen 208 can remove substances from a body lumen, such as blood, mucus, and bodily fluids that reside in the body lumen. For example, in a pulmonary procedure, catheter 200 can be extended into a main bronchus, and first lumen 208 can be used to aspirate mucus from the main bronchus. In some embodiments, second lumen 210 can deliver substances to the body lumen in which distal end portion 206 resides. For example, in some embodiments, second lumen 210 can deliver medicinal fluids in the form of liquids or aerosolized powders and/or aerosolized liquids. Such drug delivery to the lungs can be achieved by inserting distal end portion 206 of second lumen 210 into the trachea, main bronchi, lobar bronchi, segmental bronchi, and the subsegmental bronchi of the respiratory tract, and dispensing a drug into lumen 210 via port 218 at proximal end portion 204, which exits into the lung via the opening of lumen 210 at distal end portion 206. In some embodiments, first lumen 208 can deliver a fluid to flush any substances that may be clogged on first lumen 208 from aspiration. For example, a luer can be coupled to port 220, and flushing fluid can be delivered to lumen 208 via a syringe attached to the luer.

Elongated body 202 can have one of more depth indicators 222 located at proximal end portion 204. For example, depth indicators 222 can be equally spaced lines that circumscribe elongated body 202, with each indicator 222 providing a measurement of its distance to the distal end portion 206. When distal end portion 206 is inserted into a body lumen, a medical practitioner can read depth indictors 222 at proximal end portion 204 to determine the depth that distal end portion 206 has been inserted. As such, depth indicators 222 provide the medical practitioner a quick visual verification of the depth distal end portion 206 has been advanced into a body lumen.

In some embodiments, inner catheter 200 can include an acoustic device that creates a sound at distal end portion 206 of elongated body 202 for verifying the location of distal end portion 206 within a body lumen. FIGS. 3A and 3B depict a catheter 200 having an acoustic device that creates a sound at distal end portion 206 of elongated body 202 according to an embodiment. First lumen 208 can remove (e.g., aspirate) fluid in an area within a body lumen that surrounds distal end portion 206. Second lumen 210 of catheter 200 can deliver fluid, for example, a saline solution, to the area surrounding distal end portion 206. First lumen 208 can then be used to remove the fluid delivered from lumen 210 to the area surrounding distal end portion 206. This removal of the fluid can create a sound, for example, a gurgling sound, which serves as the acoustic device. Because the sound is created at distal end portion 206, identifying the location of the sound can verify the location of distal end portion 206 within a body lumen.

In some embodiments, the acoustic device can be an aerophone device, for example, a whistle, or any other device or feature of inner catheter 200 that creates a sound. As shown in FIG. 3A, a slit or edge 213 can be disposed in first lumen 208 which serves as a whistle. Slit or edge 213 is disposed at distal end portion 206 in FIG. 3A. In some embodiments, the slit or edge 213 can be disposed at proximal end portion 204. Thus, the acoustic device that creates the sound can be disposed at proximal end portion 204 or distal end portion 206. In either case, the sound is created at the opening of first lumen 208 at distal end portion 206. In particular, gas or fluid can be passed through first lumen 208, and the passing fluid or gas can go through or by slit or edge 213 causing a vibration in the fluid or gas. This vibration can create a sound at distal end portion 206. In some embodiments, the acoustic device can be a clicker or any other suitable device that can create a sound while within a body lumen.

The sound created by the acoustic device at the distal end portion of the elongated body can be detected with or without a sensing device. For example, in some embodiments, the location of the sound can be detected by using a stethoscope on an outside surface of the body in which catheter 200 is inserted. In some embodiments, the sound can be detected without using the stethoscope.

In some embodiments, instead of or in addition to an acoustic device, a light source can be disposed at distal end portion 206 of elongated body 202 for verifying the location of distal end portion 206 within a body lumen. By detecting the location of the light created by the light source, the location of the distal end portion 206 can be verified.

In one embodiment, an antenna can be disposed at distal end portion 206. The antenna is configured to emit a radio wave that can be detected from outside the body. In an embodiment, the antenna includes a metal conductor, for example, a metal band around elongated body 202 at distal end portion 206. A signal transmission line is coupled to the metal band and extends along the elongated body 202 to proximal end portion 204. The proximal end of the signal transmission wire is configured to couple to a signal transmitter that generates the radio frequency used to create the radio wave. From outside the body, a corresponding device that detects the radio waves emitted from the antenna can be used to verify the location of distal end portion 206.

In one embodiment, a metal portion can be disposed at distal end portion 206. A corresponding device that can detect the location of the metal portion (e.g., a metal detector) from outside the body can then be used to verify the location of distal end portion 206. In another embodiment, an RFID tag can be disposed at distal end portion 206. A corresponding RFID reader device that can detect the location of the RFID tag from outside the body can then be used to verify the location of distal end portion 206.

As shown in FIGS. 3A and 3B, distal end portion 106 of elongated body 102 can have a pre-formed bend that extends away from a longitudinal axis of a body lumen (see, e.g., longitudinal axis 20 shown in FIG. 8, which corresponds with longitudinal axis 20 of elongated body 102 shown in FIG. 2). In some embodiments, the pre-formed bend at distal end portion 106 of outer catheter 100 can correspond to the curvature of the body lumen(s) in which inner catheter 200 is inserted, for example, the curvature of the wind pipe (trachea 302) from the mouth or nose. As such, the pre-formed bend at distal end portion 106 of outer catheter 100 can assist in the insertion of catheter 100 through the nose or mouth to the patient's respiratory tract. Further, when catheter system 10 is configured for insertion into the trachea, the pre-formed bend at distal end portion 106 can help direct the extension of inner catheters 200a and 200b toward main bronchi 304 and 306, by helping to point extended portion of inner catheters 200a and 200b away from longitudinal axis 20 and away from carina 303 (see FIG. 9). As shown in FIGS. 3A and 3B, elongated body 102 can have a visual marker 114 that indicates a direction at which elongated body 102 curves. For example, as shown in FIGS. 3A and 3B, visual marker 114 can be a line 114 on an outer surface of elongated body 102 that is aligned with the curvature of elongated body 102. Visual marker 114 can assist the medical practitioner to adjust the rotational orientation of catheter 100 relative to the body lumen so that bent distal end portion 106 is oriented to face a desired radial direction.

In some embodiments, elongated body 202 of catheter 200 can include a pre-formed bend 205 at distal end portion 206 (see FIG. 2) that causes distal end portion 206 to extend away from a longitudinal axis 20 of a body lumen in which catheter 200 is inserted (see FIG. 10). FIGS. 1, 2, 8A, 8B, and 9 illustrate catheter 200 having an angled distal end portion 206 according an embodiment in a relaxed or confined position. (FIG. 3A is a schematic illustration that does not show pre-formed bend 205.) Angled distal end portion 206 can be flexible such that it can conform to a straight outer catheter 100 when inserted therein as illustrated in FIGS. 1 and 3B, but bend at a non-zero angle relative to longitudinal axis 20 of the body lumen when distal end portion 206 is positioned outside of distal end portion 106 of outer catheter 100. The pre-formed bend 205 can be formed by two segments of body 202 that intersect at an angle other than zero or non-180 degree angle, or any other suitable non-linear shape. In some embodiments, pre-formed bend 205 can be a curve, such that the two segments gradually angle toward each other to meet at bend 205 so as to form a curve. In some alternative embodiments, pre-formed bend 205 can be a sharp angle, such as shown in FIG. 16.

In some embodiments, distal end portion 206 of inner catheter 200 can be provided with a compound bend. FIGS. 27A and 27B illustrate inner catheter 200 having a compound bend 226 at its distal end portion 206. Compound bend 226 is distal to preformed bend 205. Compound bend 226 has a curvature that is in a direction generally opposite of the curvature of preformed bend 205. For example, as shown in FIG. 27B, preformed bend 205 can be a downward curve having a radius R1, and compound bend 226 can be an upward curve having a radius R2. Compound bend 226 and preformed bend 205 can be designed to have any degree for radii R1 and R2, which are tailored for the particular application of catheter 200. In some embodiments, radius R1 of preformed bend 205 can be from about 0.5 in. to about 2.0 in, from about 1.10 in. to about 1.50 in., or from about 0.85 in. to about 1.00 in., and radius R2 of compound bend 226 can be from about 0.10 in. to about 1.00 in, from about 0.20 in. to about 0.75 in., or from about 0.30 in. to about 0.40 in.

In some embodiments, such as shown in FIG. 27B, which is a cross-sectional view of distal end portion 206 in FIG. 27A along line 27B-27B, a marker band 215 can be embedded in the distal edge of distal end portion 206.

Elongated body 202 of inner catheter 200 and elongated body 102 of outer catheter 100 can each be made of any suitable material that provides the appropriate compromise between strength, flexibility, and other requirements. For example, suitable materials that can provide the appropriate compromise between these two extremes include silicones, polyvinylchloride (PVC), polyurethane, elastomeric polyamides, block polyamide (such as Pebax®, a polyether block amide, available from Arkema, Colombes, France), Tecoflex® and various co-polymers. In some embodiments, for each of inner and outer catheters, the desired degree of flexibility can be achieved by material selection (for example, polymers) and thickness selection. Flexibility can also be enhanced by using flexibility mechanisms such as a coiled wire 207 at bend 205 or a living hinge 209 at points were flexibility is required, or a combination thereof, for example (see later described inner catheter 200' shown in FIG. 5).

Pre-formed bend 205 of inner catheter 200 can be formed by inserting a shaped (or curved) mandrel into a lumen defined by elongated body 202 and then heating elongated body 202 with the mandrel in the lumen. After removing the mandrel, elongated body 202 can have a pre-formed bend that corresponds to the shape of the mandrel. Pre-formed bend 205 can correspond to the angle between the body lumen in which inner catheter 200 is inserted and a second body lumen that branches from the first body lumen. For example, pre-formed bend 205 can correspond to the angle between the trachea 302 and either the right or left main bronchus 304 or 306. The pre-formed bend (if provided) of outer catheter 100 can be formed using a similar method.

In some embodiments, in which two inner catheters 200 can be inserted through the lumen(s) 108 of outer catheter 100, the second inner catheter 200 can be advance independently of first inner catheter 200 or dependently with first inner catheter 200. For example, as shown in FIGS. 8A, 8B, and 9-12, a first inner catheter 200*a* can be simultaneously advanced into left main bronchus 304 while a second inner catheter 200*b* is advanced into right main bronchus 306 by virtue of pre-formed bend 205.

In addition to or in place of pre-formed bend 205, inner catheter 200 can be provided with an articulation mechanism, such as catheter pull wires as known in the art, for maneuvering distal end portion 206 to a target body lumen. Thus, in some embodiments, inner catheter 200 can be manually articulated. Where catheter system 10 includes more than one inner catheter (e.g., inner catheters 200*a* and 200*b*), catheter 200*a* and catheter 200*b* can be articulated independently of each other, which can allow distal end portion 206 to be articulated to enter a lobar bronchus 308 from a main bronchus 304 or 306 (see illustration of lung passageways in FIG. 10, for example). In some embodiments, distal end portion 206 can include location indicator(s), such as marker bands 215 that extend around the outer contour of elongated body 202 at distal end portion 206 of inner catheter 200 as shown in FIGS. 1 and 5. Marker bands 215 can be detected using imaging technology, for example, fluoroscopy or ultrasound, thereby allowing the medical practitioner to visualize the location of distal end portion 206 of inner catheter 200. The medical practitioner can articulate distal end portion 206 using pull wire(s) to enter one of the lobar bronchi 308, or deeper into a bodily passageway (e.g., segmental bronchi 310 and subsegmental bronchi).

In some embodiments, inner catheters 200*a* and 200*b* can have distinguishing location markers, thereby allowing the medical practitioner to differentiate between the two catheters 200*a* and 200*b*. For example, inner catheter 200*a* can have two marker bands 215, and inner catheter 200*b* can have three marker bands 215. Marker bands 215 can be used by the medical practitioner to verify that the inner catheters 200*a* and 200*b* are properly positioned in their respective target body lumen (e.g., left and right main bronchi 306 and 304), and that inner catheters 200*a* and 200*b* have not become twisted so as to accidentally be positioned in the respective body lumen intended for the other inner catheter. In some embodiments, distinguishing location makers can be different shapes, symbols (e.g., chevrons, which can also indicate twisting of the catheter by movement of the chevron's apex), and letters. For example, inner catheter 200*a* can have a marker 215 that is shaped as an "R," and inner catheter 200*b* can have a marker 215 that is shaped as an "L." In this example, a medical practitioner can easily recognize that the inner catheter with an "R" marker is the right inner catheter 200*a* and the inner catheter with an "L" is the left inner catheter 200*b*. For example, inner catheter 200*a* can have a marker 215 that is a chevron whose apex points left when inner catheter 200 is at one rotational orientation and whose apex then points right when inner catheter 200 is twisted about 180 degrees to another rotational orientation.

Distal end portion 106 of outer catheter 100 and distal end portion 206 of inner catheter 200 (e.g., catheters 200*a* and 200*b*) can be shaped to be atraumatic to mitigate or prevent damage to the body lumen wall in which the distal end portions are inserted. For example, the outer edges of distal tip 118 can be rounded or have a large radius curve as shown in FIGS. 4A and 4B. The distal tip 211 of distal end portion 206 of inner catheter 200 can be rounded and have a large radius as shown in FIGS. 1, 2 8A, 8B, and 9-12. FIG. 5 illustrates an inner catheter 200' which is a variation of earlier described inner catheter 200. As shown, inner catheter 200' includes an atraumatic distal tip 211' of distal end portion 206 that is bullet shaped, or conical shaped. A bullet shaped distal end portion 206 helps mitigate damage to the body lumen wall and helps guide inner catheter 200 from one body lumen into a branching body lumen. The conical shaped tip 211' can have one or more openings 207*a* and 207*b* for allowing a substance to pass through. Openings 207*a* and 207*b* can be in communication with one or more lumens in the catheter 200'. For example, in some embodiments in which inner catheter 200' has two lumens (e.g., lumens 208 and 210 in FIG. 3A), opening 207*a* can be in communication with one lumen (e.g., lumen 208), and opening 207*b* can be in communication with the other lumen (e.g., lumen 210). In such embodiments, catheter 200' can be used to deliver substances (e.g., saline or medicinal fluids) via opening 207*b* and lumen 210, and catheter 200' can be used to remove substances (e.g., aspirating mucus or other bodily fluids) via opening 207*a* and lumen 208.

Catheter 200' can include one or more flexibility mechanisms to enhance the flexibility at bend 205 or other points on elongated body 202 where flexibility is required. Such flexibility mechanisms can include, for example, coiled wire 207 or living hinge 209, or a combination thereof. In the embodiment of FIG. 5, both coiled wire 207 and living hinge 209 are provided at bend 205. Catheter 200' is also provided with a directional indicator marker 217 at proximal end portion 204, which provides the medical practitioner with a visual reference proximal end portion 204 as to what radial direction angled distal end portion 206 is pointing. When catheter 200' is configured to extend to the bronchi for aspiration, drug delivery, or other procedure (e.g., catheter 200' has a lumen for aspiration and/or a lumen for drug delivery as described above for catheter 200), indicator marker 217 clearly indicates to the medical practitioner which of the two main bronchi the distal end portion 206 resides, thereby ensuring that the procedure is conducted on the targeted lung.

In some embodiments, inner catheter 200 can also include a key joint component that corresponds to a key joint component on outer catheter 100. The corresponding key joint components can fix the rotational orientation of elongated body 202 of inner catheter 200 relative to that of elongated body 102 of outer catheter 100, and can also serve as a positional indicator as to what radial direction angled distal end portion 206 is pointing. When catheter system 10 is inserted in a body lumen (e.g., trachea), coupling the corresponding key joint components of inner and outer catheters 200 and 100 can ensure that inner catheter 200 is rotationally oriented about longitudinal axis 20 so that angled distal end portion 206 is directed toward the target branching lumen (e.g., a main bronchus). In some embodiments, the key joint components of inner catheter 200 and outer catheter 100 can be a corresponding key and keyway, respectively, or in some embodiments, a corresponding keyway and key, respectively. In some embodiments, the key joint components of inner catheter 200 and outer catheter 100 can be corresponding non-circle shapes of the contours of inner catheter 200 and outer catheter 100, for example, polygons such as squares, ovals, and any other suitable shape.

In some embodiments, the key joint components can allow limited number of different rotational orientations of elongated body 202 of inner catheter 200 relative to that of elongated body 102 of outer catheter 100. For example, outer catheter 100 can define an oval contoured lumen. An inner catheter 200 that has a corresponding contoured oval shape can be inserted in the oval contoured lumen of outer catheter 100 at a first orientation and at a second orientation that is about 180 degrees from the first orientation. As another example, outer catheter 100 can define a square contoured lumen. An inner catheter 200 that has a corresponding contoured square shape can be inserted in the square contoured lumen of outer catheter 100 at a first orientation, at a second orientation that is about 90 degrees from the first orientation, at a third orientation that is about 180 degrees from the first orientation, and at a fourth orientation that is about 270 degrees from the first orientation. It should be understood that these configurations of key joint components that allow a limited number of different rotational orientations of elongated body 202 of inner catheter 200 relative to that of elongated body 102 of outer catheter 100 are described as non-limiting examples only.

FIGS. 3A and 3B illustrate catheters 200 (specifically, catheters 200a and 200b) each having elongated body 202 with a key joint component. FIGS. 3A and 3B is schematic illustration that does not show angling of distal end portion 206 at bend 205 described above. In some embodiments, the outer contour can include a first hollow cylindrical portion 212 that defines first lumen 208, and second hollow cylindrical portion 214 that defines second lumen 210. First cylindrical portion 210 connects to a second cylindrical portion 214 along the length of elongated body 202 at intermediate portion 216. Second cylindrical portion 214 can have a smaller outer diameter than first cylindrical portion 212. The outer surface of second cylindrical portion 214 is raised from the outer surface of first cylindrical portion 212. Accordingly, second cylindrical portion 214 functions as a key joint component, and, in the particular embodiment shown, as a key. The key joint component of elongated body 202 corresponds to a key joint component on outer catheter 100 to which catheter 200 can be coupled. For example, when the key joint component on elongated body 202 is a key (as shown), the key joint component on outer catheter 100 is a keyway (as shown) that corresponds to the key on elongated body 202. Alternatively, when the key joint component on elongated body 202 is a keyway, the key joint component on outer catheter 100 is a key that corresponds to the keyway on elongated body 202.

FIGS. 6A, 6B, and 6C illustrate an inner catheter 200'', which is a variation of earlier described inner catheter 200. As shown in FIGS. 6A and 6B, inner catheter 200'' has a distal tip 211. Distal tip 211 includes a rounded ridge 224 that circumferentially extends around distal end portion 206. Inner catheter 200'' includes a first cylindrical portion 212' that defines first lumen 208, and a second, smaller cylindrical portion 214' that defines second lumen 210. Second portion 214' runs along the outer contour of first portion 212'. The distal end of second portion 214' is skived, i.e., the side profile of distal edge of second portion 214' is slanted towards first portion 212', as shown it FIGS. 6A and 6B.

FIG. 7 illustrates an inner catheter 200''', which is a variation of earlier described inner catheter 200. As shown in FIG. 7, inner catheter 200' has a distal tip 211. Distal tip 211 includes a first non-circular, for example, oval shaped as shown in FIG. 7, portion 212'' that defines first lumen 208 and defines two second lumens 210a and 210b disposed on opposite sides of first lumen 208. In still other embodiments (not shown), three or more lumens 210 can be provided.

Elongated body 102 can define a lumen 108 having an inner surface that is contoured to correspond to the contour of the outer surface of elongated body 202 of inner catheter 200. In some embodiments, as shown in FIGS. 3A and 3B, lumen 108 includes a first circular channel portion 110 and a second semicircular channel portion 112 extending outward from the periphery of first circular channel portion 110. A surface of lumen 108 forming semicircular channel portion 112 is recessed from the surface of lumen 108 forming circular channel portion 110 The radius of second semicircular portion 112 can be smaller than the radius of first circular channel portion 110. Semicircular portion 112 can function as the key joint component of catheter 100, and, in the particular embodiment shown, as the keyway that corresponds to the key on elongated body 202 of inner catheter 200. In some embodiments, first and second channel portions 110 and 112 can be semicircular shapes that together form a contour that is a circle. In some embodiments, first and second channel portions 110 and 112 can be other shapes that together form a contour that is not a circle. For example, first channel portion 110 can be circular, and second channel portion 112 can be square. In some embodiments, first and second channel portions 110 and 112 can together form other shapes such as ovals, stars, and polygons. The contour of the outer surface of elongated body 202 of inner catheter 200 corresponds with the shape of the inner surface of first and second channel portions 110 and 112.

Key joint component 214 on inner catheter 200 can be coupled with a key joint component 112 of lumen 108 in outer catheter 100, fixing the rotational orientation of inner catheter 200 relative to that of outer catheter 100 about longitudinal axis 20 of the body lumen. In some embodiments, key joint component 214 on inner catheter 200 is coupled to key joint component 112 of outer catheter 100 prior to inserting distal end portion 106 into the body lumen. In some embodiments, key joint component 214 on inner catheter 200 is coupled to key joint component 112 of outer catheter 100 after distal end portion 106 is advanced into trachea 302 by subsequently advancing catheter 200 through lumen 108.

The direction at which angled distal end portion 206 extends from the longitudinal axis 20 of the body lumen can be aligned with another body lumen that branches from the body lumen in which the outer catheter 100 is inserted, for example, left or right main bronchus 304 or 306, by rotating outer catheter 100. As noted, key components 214 and 112 can be used as a visual indicator of the rotational orientation of angled distal end portion 206. In one embodiment, the key joint component of outer catheter 100 extends along a partial length of the proximal end portion of catheter 100, for example, the embodiments further described with reference to FIGS. 17-26.

In some embodiments, the key joint component of inner catheter 200 and outer catheter 100 can extend entirely from respective proximal end portions 104 and 204 to respective distal end portions 106 and 206. In some embodiments, the key joint components of inner catheter 200 and outer catheter 100 can only extend along a partial length between respective proximal end portions 104 and 204 and distal end portions 106 and 206.

In some embodiments having two inner catheters 200a and 200b with pre-formed bends 205, the corresponding key components of inner catheters 200a and 200b with outer catheter 100 can be configured to fix the rotational orientation of inner catheters 200a and 200b relative to each other, and align the direction of each angled distal end portions 206 to be toward the target branching lumen. For example, the key components can be configured to orient the angled distal end portions 206 of catheters 200a and 200b so as to bend away from each other, as illustrated in FIG. 2. In this manner, when catheter system 10 is inserted into a body lumen such as the trachea, the rotational orientation of inner catheters 200a and 200b can be fixed relative to longitudinal axis 20 of the trachea. The angled distal end portions 206 of catheters 200a and 200b can be then be extended to easily access a respective main bronchus by virtue of the pre-formed bend 205 and fixed rotational orientation. As illustrated in the embodiments of FIGS. 8A, 8B, and 9-12, for example, when outer catheter 100 is inserted in a trachea 302, the key components of outer catheter 100 and inner catheters 200a and 200b can align distal end portion 206 of catheter 200b towards left main bronchus 304 and distal end portion 206 of catheter 200a towards right main bronchus 306. In some embodiments, inner catheters 200a and 200b are rotationally oriented so that its distal end portion 206 extends from longitudinal axis 20 of the body lumen about 180 degrees from the direction at which the distal end portion 206 of the inner catheter 200b extends from the longitudinal axis 20 of the body lumen.

FIGS. 4A-4E illustrates cross-sectional views showing exemplary catheter and lumen configurations for outer catheter 100 and inner catheter(s) 200. It should be understood that the configurations of catheter system 10 illustrated in the FIGS. 4A-4E are shown as non-limiting examples only. In FIG. 4A, the contour of the outer surface of outer catheter 100 can have an oval shape, for example. Elongated body 102 defines two circular lumens 108. Each lumen 108 receives a circular inner catheter 200a or 200b. Elongated bodies 202 of inner catheters 200a and 200b each define one lumen 208. In this configuration, in contrast with the configuration of inner and outer catheters 200a, 200b, and 100 of FIGS. 3A and 3B, inner catheters 200a and 200b of FIG. 4A are not keyed with outer catheter 100. Because inner catheters 200a and 200b are not keyed with outer catheter 100, accessories or parts at proximal end portions 204 of inner catheters 200a and 200b, for example ports 218 and 220, can be used to align the direction of pre-formed bends 205. Thus, ports 218 and 220 can serve the same purpose as direction indicator marker 217 described above with respect to the embodiment of FIG. 5.

In FIG. 4B, the contour of the outer surface of outer catheter 100 can have an oval shape, for example. Elongated body 102 defines two lumens 108 having a non-circle shape, for example, an oval. Each lumen 108 receives an inner catheter 200a or 200b having a contoured outer surface with a corresponding non-circle shape, for example, a corresponding oval shape. Elongated bodies 202 of inner catheters 200a and 200b each define two lumens 208 and 210. In this configuration, inner catheters 200a and 200b are keyed with outer catheter 100. In some embodiments, lumens 108 can be circular as shown in FIG. 4A, and inner catheters 200a and 200b can have corresponding circular contours. In such circular embodiments, outer catheter 100 would not be keyed with catheters 200a and 200b.

In FIG. 4C, the contour of the outer surface of outer catheter 100 can have a circular shape. Elongated body 102 defines one lumen 108 having a non-circle shape, for example, an oval. Lumen 108 receives an inner catheter 200 having a contoured outer surface with a corresponding non-circle shape, for example, a corresponding oval shape. Elongated body 202 of inner catheter 200 defines two lumens 208 and 210. In this configuration, single inner catheter 200 is keyed with outer catheter 100.

In FIG. 4D, the contour of the outer surface of outer catheter 100 can have a circular shape. Elongated body 102 defines one lumen 108 having a circular shape. Lumen 108 receives an inner catheter 200 having a contoured outer surface with a corresponding circular shape. Elongated body 202 of inner catheter 200 defines two lumens 208 and 210. In this configuration, single inner catheter 200 is not keyed with outer catheter 100. Accessories or parts at proximal end portion 204 of inner catheter 200, for example ports 218 and 220, can be used to align the direction of pre-formed bend 205.

In still other embodiments, lumen(s) 108 can have a triangular shape, and inner catheter 200 is provided with one lumen 208 and two lumens 210 and 210b (similar to catheter 200''' of FIG. 7). Each lumen 208, 210a, and 210b, is provided at a respective apex of the triangle as shown in the cross-sectional view of the embodiment of FIG. 4E. A method of using catheter system 10 according to some embodiments will now be described with reference to FIGS. 8A, 8B, and 9-12. In the method illustrated in FIGS. 8A, 8B, and 9-12, outer catheter 100 is inserted into a trachea 302 through the mouth or nose or by an incision in the throat. The key joint component of each inner catheter 200 is coupled with the respective key joint components of outer catheter 100. For example, the key joint components can be coupled by aligning a key on elongated body 202 of inner catheter 200 with a keyway in a lumen of outer catheter 100, and then sliding inner catheter 200 within the lumen of outer catheter 100. As illustrated in FIG. 8A, inner catheters 200a and 200b are coupled to outer catheter 100, and catheter 100 is inserted in trachea 302 and advanced through trachea 302. (FIG. 8B is similar to FIG. 8A, but illustrates inner catheters 200a and 200b having conical distal end portions 206 as described above regarding FIG. 5.) Coupling the key joint components of inner catheters 200a and 200b with the key joint components of outer catheter 100 fixes the rotational orientation of inner catheters 200a and 200b about longitudinal axis 20. The orientation of inner catheter 200a is fixed so that the direction at which pre-formed bend 205 of its distal end portion 206 extends from longitudinal axis 20 is aligned with right main bronchus 306. Similarly, the orientation of inner catheter 200b is fixed so that the direction at which the pre-formed bend of its distal end portion 206 extends from longitudinal axis 20 is aligned with left main bronchus 304. In some embodiments, outer catheter 100 can be inserted in the trachea first, and inner catheters 200a and 200b can then be slid into the lumen(s) of inner catheter 200, coupling the respective key joint components.

Returning to FIGS. 8A and 8B, outer catheter 100 with inner catheters 200a and 200b disposed therein is advanced through trachea 302. As shown in FIG. 9, distal end portions 206 of inner catheters 200a and 200b are advanced downward and towards left and right main bronchi 304 and 306. The position of outer catheter 100 is maintained in the trachea 302. Distal end portions 206 can be substantial straight (not angled relative to longitudinal axis 20 of the body lumen) while within outer catheter 100, but as distal end portions 206 extend from distal end portion 106, distal end portions 206 begin to angle away from longitudinal axis 20 as shown in FIGS. 10-12. In some embodiments, after distal end portions 206 have been advance a certain distance, pre-formed bend 205 cause distal end portions 206 to contact the side walls of trachea 302.

As shown in FIGS. 9 and 10, distal end portions 206 of inner catheters 200a and 200b can be further advanced downward and towards left and right main bronchi 304 and 306. Distal end portions 206 can slide down the side walls of trachea 302 (see FIG. 9) until the distal end portion 206 of inner catheter 200a is on the right of carina 303 at the intersection of the trachea 302 and right main bronchus 306 (see FIG. 10), and distal end portion 206 of inner catheter 200b is on the left of carina 303 at the intersection of the trachea 302 and left main bronchus 304 (see FIG. 10). A medical practitioner of catheter system 10 advances distal end portion 206 of inner catheter 200b towards left main bronchus 304 and distal end portion 206 of inner catheter 200a towards right main bronchus 306 by advancing the respective elongated bodies 202 within the lumen(s) of catheter 100.

As shown in FIG. 11, distal end portion 206 of inner catheter 200a can be advanced into right main bronchus 306, and distal end portion 206 of inner catheter 200b can be advanced into left main bronchus 304 by further advancing the respective elongated bodies 202 within the lumen(s) of catheter 100. In the embodiment shown, no articulation using pull wires of elongated body 202 is needed to advance elongated body 202 into left or right main bronchus 304 or 306. If the direction at which the pre-formed bend 205 extends away from longitudinal axis 20 of trachea 302 is aligned with the desired main bronchus, the pre-formed bend guides elongated body 202 into the desired bronchus as elongated body 202 is advanced within outer catheter 100. In some embodiments, distal end portion 206 can contact an inferior surface of the main bronchus 304 or 306 during advancement within main bronchus 304 or 306. In some embodiments, the pre-formed bend can be configured to cause distal end portion 206 to contact a superior surface of the main bronchus 304 or 306 during advancement within main bronchus 304 or 306. Distal end portions 206 of inner catheters 200a and 200b can be advanced within the main bronchi 304 and 306 until distal end portions 206 reach the intersection of the main bronchi 304 and 306 and the lobar bronchi 308.

In some embodiments, catheter system 10 can be inserted in a body lumen with one or more inner catheters 200 slightly extended from distal end portion 106 of outer catheter 100 (see, e.g., FIG. 10). Outer catheter 100 can be advanced into the body lumen until the medical practitioner feels distal end portion 206 of inner catheter(s) 200 contact a second body lumen that branches from the first body lumen, for example, left or right main bronchus 304 or 306 near carina 303. At this position, the medical practitioner can cease further advancement of outer catheter 100 and begin individual (or simultaneous, in some embodiments) advancement of each inner catheter 200. In this manner, outer catheter 100 is not advanced too far so as to mistakenly extend into one of the main bronchi, and consequently ensures that each inner catheter 200 will be advanced into the targeted main bronchus.

In some embodiments, catheter system 10 can include outer catheter 100 and a single inner catheter 200 disposed in lumen 108 defined by elongated body 102. Outer catheter 100 and inner catheter 200 are inserted into trachea 302 through the mouth or nose or by an incision in the throat. The direction at which pre-formed bend 205 extends from longitudinal axis 20 is aligned with the desired main bronchus 304 or 306. Single inner catheter 200 can be selectively deployed into either the desired main bronchus 304 and 306 by advancing elongated body 202 through elongated body 102 of outer catheter 100. As elongated body 202 of inner catheter 200 is advanced, distal end portion 206 extends away from distal end portion 106 of inner catheter 200 and begins extending away from longitudinal axis 20. During advancement of inner catheter 200, the position of outer catheter 100 can be maintained within trachea 302. Distal end portion 206 of inner catheter 200 can be advanced into the desired main bronchus 304 or 306 by further advancing elongated body 202 within lumen 108 of outer catheter 100. Pre-formed bend 205 guides elongated body 202 into the bronchus 304 or 306 aligned with the direction that pre-formed bend 205 extends from longitudinal axis 20.

In some embodiments having a single catheter 200, after distal end portion 206 has been deployed in a desired main bronchus, for example, right main bronchus 306, distal end portion 206 can be retracted from right main bronchus 306 by advancing elongated body 202 in an opposite direction. Once distal end portion 206 is out right main bronchus 306 and in trachea 302, the direction at which pre-formed bend 205 extends from longitudinal axis 20 can be realigned with left main bronchus 304 by either rotating inner catheter 200 independent from outer catheter 100 or by rotating inner catheter 200 with outer catheter 100. In some embodiments, the medical practitioner can use directional indicator marker 217 and/or key joint component 214 (if provided) to help identify and fix the rotational orientation of inner catheter 200 in trachea 302 and realign pre-formed bend 205 with left main bronchus 304. Inner catheter 200 can then be selectively deployed into left main bronchus 306 by advancing elongated body 202 through elongated body 102 of outer catheter 100 as described above. Pre-formed bend 205 guides elongated body 202 into left main bronchus 304. Afterwards, inner catheter 200 and outer catheter 100 can be removed from the body.

Catheter system 10 having only one inner catheter 200 can be useful for performing procedures in body lumens having a small diameter. For example, in pediatrics, the diameter of an infant's trachea is small and can only receive a single inner catheter 200 and endotracheal tube. In some embodiments, the endotracheal tube can serve as outer catheter 100.

In some embodiments, distal end portion 206 of inner catheter 200 can be further inserted into the lobar bronchi 308, segmental bronchi 310, and subsegmental bronchi by articulating distal end portion 206 with pull wire. In some embodiments, distal end portion 206 can include location indicator(s), such as marker bands 215, to detect the location of distal end portion 206. With location provided by the marker bands 215, a medical practitioner can articulate distal end portion 206 using pull wire(s) to angle and maneuver distal end portion 206 (in addition to the angle created by pre-formed bend 205) to enter one of the lobar bronchi 308, or deeper into a bodily passageway (e.g., segmental bronchi 310 and subsegmental bronchi).

The location of inner catheters 200a and 200b within left and right main bronchi 304 and 306, or elsewhere within the body, can be verified using acoustic devices or a light source as described above. At this point, inner catheters 200a and 200b can be used to perform various diagnostic and therapeutic procedures within the main bronchi 304 and 306, for example, deliver medicinal fluids (including, for example, aerosolized liquid or powder medicinal drugs) and/or aspirate mucus.

In some embodiments, catheter system 10 can include a catheter 400, for example, an endotracheal tube. In such embodiments, outer catheter 100 can serve as a deliver catheter for inner catheter(s) 200 while catheter 400 serves as an endotracheal tube. FIG. 12 illustrates catheter system 10, which includes catheter 400, that is inserted in trachea 302. Catheter 400 allows outer catheter 100 and inner catheter(s) 200 to be easily inserted into and removed from the trachea 302. In particular, FIG. 12 illustrates catheter 400 having an elongated body 402 and an expandable support member 420 according to an embodiment. The expandable support member 420 shown in FIG. 12 is an inflatable balloon (shown in its inflated state) mounted on an outer surface of elongated body 402. Elongated body 402 can define one or more lumens. Outer catheter 100 and inner catheter(s) 200 can pass through a lumen defined by elongated body 402. While one balloon 420 is illustrated, it should be understood that more than one balloon 420 can be provided along the length of body 402 of catheter 400. Such balloon (s) 420 can serve to selectively engage the body lumen and further secure catheter 400 in position in trachea 302, for example, at the center of trachea 302. Because catheter 400 is secured in position in trachea 302, catheter 400 can also help position outer catheter 100 and inner catheter(s) 200 at a desired location within the body lumen by passing outer catheter 100 and inner catheter(s) through a lumen in elongated body 402 of catheter 400.

Balloon 420 can be donut-shaped so as to have a circular body 421 with a central axial opening. Elongated body 402 extends through the axial opening of the balloon 420. The inflatable balloon can be filled by any suitable gas or liquid, for example, air. When the balloon 420 is inflated to contact the wall of a body lumen and stabilize elongated body 402, balloon 420 and elongated body 402 can occlude the body lumen, but a lumen defined by elongated body 402 permits the continued passage of bodily fluid or gas through the body lumen via the lumen of elongated body 402. For example, inhaled or exhaled air through the trachea 302 or main bronchi 304 and 306 is permitted with minimal obstruction by the presence of catheter 400 having a catheter system 10 coupled thereto, thereby reducing or eliminating the likelihood that the catheterization will detrimentally affect the patient's natural bodily functions. In some embodiments, expandable support member 420 can be a non-inflatable, mechanical expandable support member (e.g., formed of a shape-memory material) such as described in U.S. patent application Ser. No. 12/873,977. Exemplary expandable support members that can be employed as expandable support member(s) 420 are described in U.S. patent application Ser. No. 12/873,977, filed Sep. 1, 2010, which is incorporated by reference in its entirety herein.

In some embodiments, catheter 400 can have one balloon 420 that is an inflatable babble on one side of elongated body 402. In some embodiments, catheter 400 can have two balloons 420 that are inflatable bubbles on opposite sides of elongated body 402.

In embodiments using catheter 400 as shown in FIG. 12, catheter 400 can be inserted in trachea 302 inserted into a trachea 302 through the mouth or nose or by an incision in the throat. Outer catheter 100 and inner catheter(s) 200 can pass through a lumen defined by elongated body 402 of catheter 400 and advanced in a trachea 302 as described above regarding FIGS. 8B, 8B, and 9. Inner catheter(s) 200 can then be deployed as described above regarding FIGS. 9-11. After performing a desired procedure (e.g., aspiration of the lungs), outer catheter 100 and inner catheter(s) 200 can be withdrawn from the body while catheter 400 remains in place within trachea 302.

In some embodiments, catheter 400, outer catheter 100, and inner catheter(s) 200 can be inserted in a body lumen with one or more inner catheters 200 slightly extended from the distal end portion 106 of outer catheter 100 (see, e.g., FIG. 10) and from the distal end of elongated body 402. Catheter 400, outer catheter 100, and inner catheter(s) 200 can then be simultaneously advanced into the body lumen until the medical practitioner feels distal end portion 206 of inner catheter(s) 200 contact a second body lumen that branches from the first body lumen, for example, right or left main bronchus 304 or 306 near carina 303. At this position, the medical practitioner can cease further advancement of catheter 400 and outer catheter 100, and begin individual (or simultaneous, in some embodiments) advancement of each inner catheter(s) 200. In this manner, catheter 400, as well as outer catheter 100, is not advanced too far so as to mistakenly extend into the second body lumen, for example, one of the main bronchi, and consequently ensures that each inner catheter(s) 200 will be advanced into the targeted bronchus. In some embodiments, when advancement of catheter 400 is stopped, expandable support member 420 is engaged with the side wall of the body lumen to secure catheter 400 in place within the body lumen, as shown in FIG. 12.

For example, catheter system 10 can include outer catheter 100 and two inner catheters 200a and 200b slidably disposed therein in one or more lumen(s) 108. Outer catheter 100 and two inner catheters 200a and 200b can pass through catheter 400 (if provided) which is inserted in a patient's mouth or an incision in the throat. The direction at which pre-formed bend 205 of inner catheter 200a extends from longitudinal axis 20 is aligned with right main bronchus 306, and the direction at which pre-formed bend 205 of inner catheter 200b is aligned with left main bronchus 304. Catheter 400, outer catheter 100, and inner catheters 200a and 200b, each having a distal end portion 206 slightly extended from distal end portion 106 of outer catheter 100, can then be simultaneously advanced into trachea 302 until the medical practitioner feels distal end portions 206 of inner catheters 200a and 200b contact right and left main bronchi 306 and 304. At this position, the medical practitioner can cease further advancement of catheter 400 and outer catheter 100. In this manner, catheter 400, as well as outer catheter 100, is not advanced too far so as to mistakenly extend into one of the main bronchi 306 or 304, and consequently ensures that each inner catheter 200a and 200b will be advanced into the targeted bronchus 306 and 304, respectively. In addition, by virtue of inner catheters 200a and 200b each being advanced in a different main bronchus, the medical practitioner can be prevented from advancing catheters 400 and 100 past carina 303 into one of the main bronchi. Moreover, the inner catheter 200a and 200b being in a different main bronchus helps properly position outer catheter 100 and catheter 400 in trachea 302, thereafter the expandable member can be inflated (e.g., expandable member 420 for the embodiment of FIG. 12 having catheter 400, or expandable member 120 for the later-described embodiment of FIG. 13).

Inner catheters 200a and 200b can be advanced into the main bronchi 306 and 304, respectively, by simultaneously advancing elongated body 202 of inner catheter 200a and elongated body 202 of inner catheter 200b within elongated body 102 of outer catheter 100. As elongated bodies 202 of inner catheters 200a and 200b are advanced, distal end portions 206 of inner catheters 200a and 200b extend away from distal end portion 106 of inner catheter 200 and begin extending away from longitudinal axis 20. During advancement of inner catheters 200a and 200b, the position of outer catheter 100 can be maintained within trachea 302. Distal end portions 206 of inner catheters 200a and 200b can be advanced into main bronchus 306 and 304, respectively, by further advancing elongated bodies 202 of inner catheters 200a and 200b within lumen(s) 108 of outer catheter 100. Pre-formed bend 205 of inner catheter 200a guides elongated body 202 of inner catheter 200a into right main bronchus 306, and pre-formed bend 205 of inner catheter 200b guides elongated body 202 of inner catheter 200b into left main bronchus 304.

After performing the desired procedures in left and right main bronchi 304 and 306 (or in a further branching bronchi, if distal end portions are articulated deeper), inner catheters 200a and 200b, along with outer catheter 100, can be withdrawn from the body while catheter 400 remains in place within trachea 302 (and secured in position via expandable member 420). Outer catheter 100 and inner catheters 200a and 200b can be reinserted into the body through catheter 400 to perform another procedure, for example, aspiration of target bronchi, when needed.

In some embodiments, catheter system 10 can include outer catheter 100 and one or more inner catheters, and outer catheter 100 can be provided with one or more expandable support member(s) 120 (similar to balloon 420 provided with catheter 400), which secure outer catheter 100 in place in a body lumen, for example, a trachea or a main bronchus. In such embodiments, outer catheter 100 can serve as an endotracheal tube, for example (in lieu of a separate catheter 400 serving as an endotracheal tube as described above with reference to FIG. 12). Support member(s) 120 can be expanded once distal end portion 106 has been advance through trachea 302 to the desired position within as illustrated in FIG. 13. In particular, FIG. 13 illustrates catheter system 10 having outer catheter 100 with expandable support member 120 according to an embodiment. The expandable support member 120 shown in FIG. 13 is an inflatable balloon (shown in its inflated state) mounted on an outer surface of elongated body 102. While one balloon 120 is illustrated, it should be understood that more than one balloon 120 can be provided along the length of body 102 of catheter 100, which can serve to engage the body lumen and further secure catheter 100 in position. The inflatable balloon can be filled by any suitable gas or liquid, for example, air.

In some embodiments, outer catheter 100 and inner catheter(s) 200 can be inserted in a body lumen with one or more inner catheters 200 slightly extended from the distal end portion 106 of outer catheter 100 (see, e.g., FIG. 13). Outer catheter 100 and inner catheter(s) 200 can then be simultaneously advanced into the body lumen until the medical practitioner feels distal end portion 206 of inner catheter(s) 200 contact a second body lumen that branches from the first body lumen, for example, right or left main bronchus 304 or 306 near carina 303. At this position, the medical practitioner can cease further advancement of outer catheter 100, and begin individual (or simultaneous, in some embodiments) advancement of inner catheter(s) 200. In this manner, outer catheter 100 is not advanced too far so as to mistakenly extend into the second body lumen, for example, one of the main bronchi, and consequently ensures that inner catheter(s) 200 will be advanced into the targeted bronchus. In some embodiments, when advancement of outer catheter 100 is stopped, expandable support member 120 is engaged with the side wall of the body lumen to secure outer catheter 100 in place within the body lumen, as shown in FIG. 13. After performing the desired procedures in left and right main bronchi 304 and 306 (or in a further branching bronchi, if distal end portions are articulated deeper), inner catheter(s) 200 can be withdrawn from the body while outer catheter 100 remains in place within trachea 302 (and secured in position via expandable member 120). Inner catheter(s) 200 can be reinserted into the body through outer catheter 100 to perform another procedure, for example, aspiration of target bronchi, when needed.

In some embodiments, balloon 120 can completely occlude the gap between elongated body 102 and the side wall of trachea 302. In such embodiments, ventilation can occur through one or more lumens defined by elongated body 102. For example, inhaled or exhaled air through the trachea 302 or primary bronchi 304 and 306 is permitted with minimal obstruction by the presence of the lumen(s) in outer catheter 100 secured in place with inflated balloon 120, thereby reducing or eliminating the likelihood that the catheterization will detrimentally affect the patient's natural bodily functions. In other words, outer catheter 100 can also function as an endotracheal tube that establishes and maintains an airway that allows the passage of oxygen and carbon dioxide through trachea 302. In some embodiments, expandable support member 120 can be a non-inflatable, mechanical expandable support member (e.g., formed of a shape-memory material) such as described in U.S. patent application Ser. No. 12/873, 977. Exemplary expandable support members that can be employed as expandable support member(s) 120 are described in U.S. patent application Ser. No. 12/873,977, filed Sep. 1, 2010.

Accordingly, a medical practitioner using a catheter system 10 and method as described above can easily intubate left and right main bronchi 306 and 304 with inner catheters 200b and 200a without using an endoscopic procedure to ensure that the working catheter has actually entered left and right main bronchi 306 and 304.

Also, for example, FIG. 14 illustrates an outer catheter 100' which is a variation of earlier described outer catheter 100. As shown, outer catheter 100' includes an elongated body 102' that defines two channels 108'. Channels 108' can be separated by divider 109' formed in elongated body 102'. Distal end portion 106 can comprise a closed cap 121. Cap 121 can form an atraumatic tip, for example, a conical shape or rounded edge. Cap 121 can have openings 122a and 122b on the side walls of cap 121. Channels 108' can terminate proximal to openings 122a and 122b on the side walls of cap 121. Distal end portions 206 of inner catheters 200a and 200b will pass through openings 122a and 122b in cap 121 as catheters 200a and 200b are advanced because pre-formed bends 205 in distal end portions 206 (see, e.g., FIG. 2) biases distal end portions 206 towards the side wall. Once distal end portions 206 reach respective openings 122a and 122b, distal end portions 206 extend through openings 122a and 122b. Inner catheters 200a and 200b can then be deployed in a body lumen as described above regarding FIGS. 8A, 8B, and 9-12. Further, for example, FIG. 15 illustrates an outer catheter 100'' which is a variation of earlier described outer catheter 100. As shown, outer catheter 100'' includes an elongated body defines a first lumen 108a and a second lumen 108b through which inner catheters 200a and 200b, respectively pass. First lumen 108a has an opening 122a' on the side wall of elongated body 102. Second lumen 108b has an opening 122b' at the distal tip of distal end portion 106. Distal end portion 206 of inner catheter 200a will pass through opening 122a on the side wall of elongated body 102 as catheter 200a is advanced because pre-formed bend 205 in distal end portion 206 (see, e.g., FIG. 2) of catheter 200a biases distal end portion 206 towards the side wall of lumen 108 having opening 120b'. Once distal end portion 206 of inner catheter 200a reaches opening 122b', distal end portion 206 of catheter 200a extends through opening 122b'. Inner catheter 200a can then be deployed in a body lumen as described above regarding FIGS. 8A, 8B, and 9-12. Similarly, distal end portion 206 of inner catheter 200b will pass through opening 122h at the distal tip of distal end portion 106 as catheter 200b is advanced as described above in FIGS. 8A, 8B, and 9-12. In some embodiments, outer catheters 100' and 100'', as shown in FIGS. 14 and 15, can be used with catheter 400.

As discussed above regarding FIGS. 3A and 3B, inner catheters 200a and 200b can define one or more lumens having an opening at proximal end portion 204 and an opening at distal end portion 206. For example, elongated body 202 can define a first lumen 208 and a second lumen 210 that extend from proximal end portion 204 to distal end portion 206. First lumen 208 can remove substances from a body lumen, such as blood, mucus, and bodily fluids that reside in the body lumen. For example, in a pulmonary procedure, catheter 200 can be extended into a main bronchus, and first lumen 208 can be used to aspirate mucus from the main bronchus. In some embodiments, second lumen 210 can deliver substances to the body lumen in which distal end portion 206 resides. For example, in some embodiments, second lumen 210 can deliver medicinal fluids in the form of liquids or aerosolized powders and/or aerosolized liquids.

In one embodiment, as illustrated in FIG. 16, inner catheter 200 includes distal end portion 206 having pre-formed bend 205 that forms a sharp angle $\alpha$. Angle $\alpha$ between distal end portion 206 and elongated body 202 at bend 205 can be any value from about 90 to about 180 degrees. As shown, port 218 disposed on the same side to which distal end portion 206 bends, and thus can serve the same purpose as direction indicator marker 217 described above with respect to the embodiment of FIG. 5.

FIG. 17 illustrates a side view of catheter system 10 according to an embodiment. Catheter system 10 includes outer catheter 100 as described above in various embodiments, an inner catheter 200 slidably disposed within a lumen of the outer catheter 100 as described above in various embodiments, and a fitting 500.

In one embodiment, outer catheter 100 is an endotracheal tube having a lumen extending from proximal end portion 104 to distal end portion 106. Outer catheter 100 includes an expandable member 120 at distal end portion 106. Expandable member 120 is configured to selectively expand to brace outer catheter 100 within a body lumen. Outer catheter 100 also includes a port 124 and tube 126 in fluid communication with expandable member 120. Port 124 is configured to be coupled to a liquid supply via a pump for supplying a liquid (e.g., saline) to port 124 and tube 126. Alternatively, gas (e.g., air) may be supplied to port 124 and tube 126 via a gas pump. Accordingly, liquid or gas can be passed through port 124 and tube 126 into expandable member 120 to expand expandable member 120.

In an embodiment, outer catheter 100 includes fitting 500 coupled to proximal end portion 104 of elongated body 102. Fitting 500 includes a distal portion 502 and a branched proximal portion that includes a first proximal portion 504 and a second proximal portion 506 branched from first proximal portion 504. Distal portion 502 can define a hollow chamber that generally corresponds to the outer contour of proximal end portion 104 of elongated body 102. The proximal tip of proximal end portion 104 can be seated within the chamber of distal portion 502. In another embodiment, not shown, fitting 500 can include a third proximal portion branched from first proximal portion 504.

First proximal portion 504 includes the first key joint component of outer catheter 100. FIG. 18 illustrates a cross-sectional view of proximal portion 504 taken along line 18-18 of FIG. 17. In one embodiment, as shown in FIG. 18, proximal portion 504 includes a hollow cylindrical portion 508 and a cap 510 at a bottom end of hollow cylindrical portion 508. Cap 510 defines an opening 512. Opening 512 and the chamber defined by cylindrical portion 508 are in communication with a lumen of outer catheter 100. Accordingly, inner catheter 200 can slide through opening 512 such that distal end portion 206 extends from distal end portion 106 of outer catheter 100. The first key joint component of outer catheter 100 can include opening 512. For example, opening 512 can have a non-circular shape, for example, polygons such as squares, ovals, curvi-linear shapes such as a D-shape, and any other suitable non-circular shape. The outer contour of inner catheter 200 corresponds to the non-circular shape of opening 512. In one embodiment, opening 512 can be D-shaped as shown in FIG. 18. In other embodiments, opening 512 can be oval-shaped as in later described FIG. 19B, or other suitable shapes such as such as those described above.

In one embodiment, first proximal portion 504 can be selectively rotated relative to distal portion 502. Accordingly, the orientation of opening 512 rotates along with proximal portion 504, which allows a medical practitioner to selectively change the direction at which distal end portion 206 of catheter 200 will extend from distal end portion 106 of outer catheter 100 when catheter 200 is inserted through opening 512 and through outer catheter 100.

As shown in FIG. 18, elongated body 202, defining first lumen 208 and second lumen 210, extends through opening 512. The outer contour of elongated body 202 corresponds to the D-shape of opening 512, preventing rotation of catheter 200 relative to opening 512 and, thus, catheter 100.

Fitting 500 also includes a second proximal portion 506 in some embodiments. Second proximal portion 506 can define an opening 507 in communication with the same lumen as opening 512 or in communication with a second lumen of outer catheter 100. In one embodiment, second proximal portion 506 can be configured to couple to a ventilator.

In an embodiment, fitting 500 is configured to selectively couple to proximal end portion 104 of elongated body 102. For example, distal portion 502 can define an inner chamber (see FIG. 19) sized for a press fit with proximal end portion 104 of elongated body 102. For example, in some embodiments, fitting 500 can be configured to fit endotracheal tubes that have an outer diameter ranging from about 4 mm to about 10 mm, and in one embodiment, fitting 500 can be configured to fit endotracheal tubes having an outer diameter of about 8.5 mm.

In an embodiment, an inner surface of distal portion 502 can have threads that correspond to threads on an outer surface of proximal end portion 104. In such embodiment, fitting 500 is threaded on proximal end portion 104 of outer catheter 100.

In one embodiment, a kit for use with a conventional endotracheal tube includes fitting 500 as described above. Fitting 500 selectively couples to the endotracheal tube. The kit can include first inner catheter 200 (e.g., inner catheter 200a or 200b) as described above. In one embodiment, the kit also includes second inner catheter 200 (e.g., inner catheter 200b or 200a) that has a distal end portion that extends at a different direction than the distal end portion of the first inner catheter relative to an outer surface of the outer catheter. The kit can also include instructions for using the fitting 500 and inner catheter(s) 200 with an outer catheter 100 such as a conventional endotracheal tube. In an embodiment, the kit includes a pair of sterilized gloves to be used by the practitioner.

As shown in FIG. 17, first proximal portion 504 having the key joint component, including opening 512, is not axially aligned with elongated body. First proximal portion 504 is angled from proximal end portion 104 and distal portion 502.

FIGS. 19A-19C illustrate catheter system 10 according to an embodiment. As shown in FIGS. 19A-19C, catheter system 10 includes fitting 500. As shown in FIG. 19A, which is a side view of catheter system 10, first proximal portion 504 having the key joint component is axially aligned with proximal end portion 104 of outer catheter 100, i.e., first proximal portion 504 is not angled relative to proximal end portion 104. FIG. 19B illustrates a back view of fitting 500. As shown in FIG. 19B, opening 512 is oval-shaped. FIG. 19C is a cross-sectional view of fitting 500 taken along line 19C-19C of FIG. 19A. Proximal portion 504 includes cylindrical portion 508 and cap 510. Cap 510 defines opening 512. As shown in FIG. 19C, cap 510 is integral with cylindrical portion 508 and fitting 500. In other embodiments (not shown), cap 510 can be a separate member that is detachable from the remaining body of fitting 500. For example, cap 510 can be sized for a press or snap fit within the chamber defined by cylindrical portion 508 (as shown in FIG. 20C). As shown in FIG. 19C, distal portion 502 includes an outer cylindrical wall 514 and an inner, concentric cylindrical wall 516. Outer and inner cylindrical walls 514 and 516 collectively define a chamber 518. Inner cylindrical wall 516 defines a chamber 520 in communication with opening 512. Chamber 518 is sized to closely receive proximal portion 104 of outer catheter 100 for a press fit. Accordingly, fitting 500' can be selectively attached to outer catheter 100. In another embodiment, cap 510 can be selectively rotated relative to cylindrical portion 508. As cap 510 rotates, the orientation of opening 512 rotates, which allows a medical practitioner to selectively change the direction at which distal end portion 206 of catheter 200 will extend from outer catheter 100.

In one embodiment, outer catheter 100 with fitting 500 can have a second key joint component. For example, FIGS. 20A and 20B illustrate fitting 500 having a second key joint component. As shown in FIGS. 20A and 20B, proximal portion 504 includes cap 510. Cap 510 defines a first opening 512a and a second opening 512b. First and second openings 512a and 512b can have any suitable non-circular shape, for example, an oval shape as shown in FIG. 20A. The first key joint component can include first opening 512a defined by cap 510, and the second key joint component can include second opening 512b defined by cap 510 of proximal portion 504. In one embodiment, as shown in FIG. 20A, second opening 512b has the same non-circular shape as first opening 512a, for example, an oval shape (as shown in FIG. 20A) or D-shape as illustrated in FIG. 18. As shown in the embodiment of FIG. 20B, cap 510 is integral with cylindrical portion 508 and fitting 500.

As shown in the embodiment of fitting 500 of FIG. 20C, cap 510 is a separate member and is not integral with cylindrical wall 208 or any other portion of fitting 500. Cap 510 can be sized for a press or snap fit within the chamber defined by cylindrical portion 508. For example, as shown in FIG. 20C, the circumferential outer surface of cap 510 can tightly contact the inner surface of cylindrical portion 508. In one embodiment, separate cap 510 is selectively coupled to cylindrical portion 508 of fitting 500.

In some embodiments, the non-circular shape of second opening 512b can have an orientation that is rotated relative to the orientation of first opening 512a. For example, second opening 512b can have an orientation that is rotated about 180 degrees from the orientation of first opening 512a. In other embodiments, second opening 512b is rotated at other suitable degrees, for example, more than about 45 degrees, more than about 90 degrees, more than about 135 degrees relative to the orientation of first opening 512a. Accordingly, when the same inner catheter 200 having an angled distal end portion 206 is inserted through second opening 512b, the angled distal end portion 206 will point in a different direction than the direction it points when the inner catheter 200 passes through first opening 512a.

A method of using catheter system 10 including a fitting 500 according to some embodiments will now be described with reference to FIGS. 18 and 22-25. In the method illustrated in FIGS. 22-25, catheter system 10 includes outer catheter 100, inner catheter 200a, and inner catheter 200b. Inner catheter 200a and inner catheter 200b have the same non-circular outer contour, but distal ends 206 of each inner catheter 200a and 200b extend in different directions due to the orientation of preformed bends 205 relative to elongated bodies 202. In some embodiments, the angle between the direction the distal end portion 206 of inner catheter 200a extends is about 180 degrees from the direction the distal end portion 206 of inner catheter 200b extends. In some embodiments, the angle is more than about 45 degrees, more than about 90 degrees, or more than about 135 degrees.

In operation, distal end 106 of outer catheter 100 is inserted into trachea 302 through the mouth or nose or by an incision in the throat (see FIG. 22). In one embodiment, outer catheter 100 is an endotracheal tube that allows inner catheter 200 to be easily inserted into and removed from trachea 302. In particular, FIG. 22 illustrates outer catheter 100 having an elongated body 102 and an expandable support member 120 according to an embodiment. The expandable support member 120 shown in FIG. 22 is an inflatable balloon (shown in its inflated state). Inner catheter 200 passes through a lumen defined by elongated body 102.

Fitting 500 (not shown in FIGS. 22-25) can be coupled to proximal end portion 104 of outer catheter 100 outside the body before or after catheter 100 is inserted into trachea 302. The key joint component of inner catheter 200a, e.g., the non-circular outer contour of elongated body 202, is coupled with the respective key joint component of outer catheter 100 on fitting 500, for example, the non-circular shaped opening 512. Particularly, the key joint components can be coupled by aligning the shape of elongated body 202 of inner catheter 200a with the shape of opening 512 in fitting 500, and then sliding inner catheter 200a through opening 512 and through the lumen of outer catheter 100. Coupling the key joint component of inner catheter 200a with the key joint component of fitting 500 fixes the rotational orientation of inner catheter 200 about longitudinal axis 20. The orientation of inner catheter 200a is fixed so that the direction at which pre-formed bend 205 of its distal end portion 206 extends from longitudinal axis 20 is aligned with a main bronchus, for example, right main bronchus 306.

As shown in FIG. 24, distal end portion 206 of inner catheter 200a is advanced downward and towards right main bronchus 306. The position of outer catheter 100 is maintained in the trachea 302. Distal end portion 206 can be substantial straight (not angled relative to longitudinal axis 20 of the body lumen) while within outer catheter 100 (see FIG. 23), but as distal end portion 206 extends from distal end portion 106, distal end portion 206 begins to angle away from longitudinal axis 20 (see FIGS. 23 and 24).

As shown in FIGS. 23 and 24, distal end portion 206 of inner catheter 200a is further advanced downward and towards right main bronchus 306. Distal end portion 206 can slide down the side wall of trachea 302 (see FIG. 24) until distal end portion 206 of inner catheter 200a is on the right of carina 303 at the intersection of trachea 302 and right main bronchus 306 (see FIG. 24). A medical practitioner of catheter system 10 advances distal end portion 206 of inner catheter 200a towards right main bronchus 306 by advancing elongated body 202 within the lumen of catheter 100.

As shown in FIG. 24, distal end portion 206 of inner catheter 200a can be advanced into right main bronchus 306. In the embodiment shown, no articulation using pull wires of elongated body 202 is needed to advance elongated body 202 into right main bronchus 306. If the direction at which the pre-formed bend 205 extends away from longitudinal axis 20 of trachea 302 is aligned with the desired main bronchus, the pre-formed bend guides elongated body 202 into the desired bronchus as elongated body 202 is advanced within outer catheter 100. Distal end portion 206 can then be advanced to a target location with the main bronchi or lobar bronchi. In some embodiments having an antenna at distal end portion 206, a device configured to detect a radio signal emitted from the antenna can be used to verify that the distal end portion 206 is in the desired main bronchus.

Once distal end portion 206 is advanced to the target location, inner catheter 200a can be used for a pulmonary procedure, for example, aspirating mucus from the main bronchus through lumen 208. In some embodiments, second lumen 210 can deliver substances to the body lumen in which distal end portion 206 resides. For example, in some embodiments, second lumen 210 can deliver medicinal fluids in the form of liquids or aerosolized powders and/or aerosolized liquids. In some embodiments, a saline solution can be delivered through lumen 210 while aspirating the mucus through lumen 208. The saline solution breaks up the mucus, making aspiration easier and/or more effective.

In some embodiments, as shown in FIG. 24, distal end portion 206 can contact an inferior surface of right main bronchus 306 during advancement within right main bronchus 306. Distal end portion 206 of inner catheter 200a can be advanced within the main bronchus 306 until distal end portions 206 reaches the intersection of right main bronchus 306 and the lobar bronchi 308.

After distal end portion 206 of inner catheter 200a has been deployed in right main bronchus 306, distal end portion 206 can be retracted from right main bronchus 306 by advancing elongated body 202 in an opposite, proximal direction. Once distal end portion 206 of inner catheter 200a is retracted from right main bronchus 306, and taken out of trachea 302, outer catheter 100, and fitting 500, the key joint component of inner catheter 200b, e.g., the non-circular outer contour of elongated body 202, is coupled with opening 512 of fitting 500 by aligning the shape of elongated body 202 of inner catheter 200b with the shape of opening 512 in fitting 500, and then sliding inner catheter 200b through opening 512 and through the lumen of outer catheter 100. Coupling the key joint component of inner catheter 200b with the key joint component of fitting 500 fixes the rotational orientation of inner catheter 200b about longitudinal axis 20. Because inner catheter 200b is configured so that distal end portion 206 of inner catheter 200b extends from the longitudinal axis 20 at a different direction than that of distal end portion 206 of inner catheter 200a, the orientation of inner catheter 200b is fixed so that the direction at which its distal end portion 206 extends from longitudinal axis 20 can be aligned with left main bronchus 304.

Inner catheter 200b can then be selectively deployed into left main bronchus 304 by advancing elongated body 202 through elongated body 102 of outer catheter 100 as described above regarding inner catheter 200a. Pre-formed bend 205 guides elongated body 202 of inner catheter 200b into left main bronchus 304 as shown in FIG. 25.

In some embodiments, distal end portions 206 of inner catheters 200a and 200b can be further inserted into the lobar bronchi, segmental bronchi, and subsegmental bronchi by articulating distal end portion 206 with a pull wire.

In some embodiments, second inner catheter 200b is unnecessary. For example, after distal end portion 206 of inner catheter 200a has been deployed in right main bronchus 306, distal end portion 206 can be retracted from right main bronchus 306 by advancing elongated body 202 in an opposite, proximal direction. Then the orientation of opening 512 can be rotated, for example, about 180 degrees, relative to elongated body 102. In one embodiment, the entire fitting 500 can be rotated relative to elongated body 102 of outer catheter 100. For example, fitting 500 can be removed from proximal end portion 104 of catheter 100, rotated relative to catheter 100, and recoupled to proximal end portion 104. In another embodiment, fitting 500 can be rotated while remaining attached to proximal end portion 104. In another embodiment in which cap 510 (which defines opening 512) is attached to (rather than being integral with) cylindrical portion 508 as shown in FIG. 20C, cap 510 can then be rotated relative to cylindrical portion 508. In this embodiment, fitting 500 can remain coupled to inner catheter 100, while cap 510 is rotated relative to cylindrical portion 508. Accordingly, the direction at which distal end portion 206 extends from longitudinal axis 20 is different than the direction it extends before rotating the orientation of opening 512. At this second orientation, the direction at which distal end portion 206 extends is aligned with the other main bronchus, for example, left main bronchus 304. Inner catheter 200a can then be advanced into left main bronchus 304 as described above.

In another embodiment in which fitting 500 includes a second key joint component, second inner catheter 200b is unnecessary. For example, fitting 500 can define first opening 512a and second opening 512b as shown in FIGS. 20A and 20B. In such embodiments, after distal end portion 206 of inner catheter 200a has been deployed in right main bronchus 306, distal end portion 206 can be retracted from right main bronchus 306 by advancing elongated body 202 in an opposite, proximal direction. Then, the key joint component of inner catheter 200a can be coupled with the second key joint component of fitting 500, for example, second oval-shaped opening 512b. Particularly, the key joint component of inner catheter 200a can be coupled by aligning the shape of elongated body 202 of inner catheter 200a with the shape of second opening 512b in fitting 500, and then sliding inner catheter 200a through second opening 512b and through the lumen of outer catheter 100. Coupling the key joint component of inner catheter 200a with the second key joint component of fitting 500 fixes the rotational orientation of inner catheter 200 about longitudinal axis 20. If the orientation of second opening 512b is rotated from the orientation of first opening 512, e.g., about 180 degrees, the orientation of inner catheter 200a is fixed so that the direction at which distal end portion 206 extends from longitudinal axis 20 is aligned with the other main bronchus, for example, left main bronchus 304.

In some embodiments in which a second key joint component is provided, second inner catheter 200b with the same configuration as inner catheter 200a is used. Second inner catheter 200b is coupled to the second key joint component (e.g., opening 512b) while first inner catheter 200a is coupled to the first key joint component (e.g., opening 512a) of the same lumen (or in some embodiments, respective lumens) of outer catheter 100. Thus, first and second inner catheters 200a and 200b can be deployed into the right and left main bronchi at the same time to allow aspiration of both lungs without having to reposition inner catheter 200a from one main bronchus into the other main bronchus. Moreover, employing two inner catheters 200a and 200b in lumen(s) of outer catheter 100 can further be used to properly place outer catheter 100 in trachea 302, as described above with reference to FIG. 13.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. For example, although the figures illustrate the catheter system in the respiratory tract, the catheter system can be adapted for other body lumens such as the vascular system. Also, for example, FIGS. 21A and 21B illustrate a catheter system including a variation of earlier described outer catheter 100. As shown, outer catheter 100 also includes a second lumen terminating at opening 128. Opening 128 is proximal of expandable member 120. The second lumen is in communication with port 130 and tube 132. Port 130 is configured to be coupled to a suction source. Accordingly, in operation, a portion of the body lumen proximal of expandable member 120 can be aspirated through opening 128.

Further, for example, FIG. 26 illustrates catheter system 10 including a variation 500' of earlier described fitting 500. As shown in FIG. 26, fitting 500' can further include a third proximal portion 522. First proximal portion 504 can include a non-circular opening 512, as described above with reference to FIGS. 17, 18, and 19A. In one embodiment, second proximal portion 506 can have a rubber gasket and be configured for inserting an instrument, for example, a bronchoscope, through a lumen of outer catheter 100. In another embodiment, second proximal portion 506 can include a key joint component, including a non-circular opening 512, as described above with reference to FIGS. 17, 18, and 19A. The non-circular opening 512 of second proximal portion 506 can have an orientation that is rotated relative to the orientation of opening 512 of first proximal portion 504 such that when the same inner catheter 200 having an angled distal end portion 206 is inserted through the opening of third proximal portion 522, the angled distal end portion 206 will extend in a different direction than the direction it extends when the inner catheter 200 passes through the opening of first proximal portion 504. In another embodiment, second proximal portion 506 can define two openings 512a and 521b as described above with reference to FIGS. 20A-20C to receive first inner catheter 200a and second inner catheter 200b as described above regarding FIGS. 1 and 2. Third proximal portion 522 can be configured to couple with a ventilator. Thus, using fitting 500', a practitioner can access one lung using a single catheter 200 or access both lungs using inner catheter(s) 200, while also providing an opening for inserting a bronchoscope and an opening for coupling with a ventilator.

It should be understood that any features of an embodiment disclosed herein can be combined with any features of any other embodiment disclosed herein, without departing from the scope of the present disclosure Thus, for example, any of the features of fitting 500 described above can be combined with any features of fitting 500' described herein with reference to FIG. 26.

Therefore, such adaptations and modifications are intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

What is claimed is:

1. An aspiration catheter system comprising:
    a first catheter including a first proximal end, a first elongated body, a first distal end, and a first lumen extending through the first elongated body from the first proximal end to the first distal end, the first proximal end comprising a fitting that defines a first opening and a second opening, the first opening being D-shaped to form a first key joint component, and the second opening being D-shaped to form a second key joint component;
    a second catheter including a second elongated body, a second distal end, a second proximal end, a second lumen extending through the second elongated body to the second distal end, a pre-formed bend proximal to the second distal end, and a third key joint component that corresponds with the first key joint component, the third key joint component being defined by a D-shaped cross-section of the second catheter that corresponds to the D-shape of the first opening of the first key joint component; and
    a third catheter including a third elongated body, a third distal end, a third proximal end, a third lumen extending through the third elongated body, a pre-formed bend proximal to the third distal end, and a fourth key joint component that corresponds with the second key joint component, the fourth key joint component being defined by a D-shaped cross-section of the third catheter that corresponds to the D-shape of the second opening of the second key joint component,
    wherein the first key joint component and the third key joint component are configured to be coupled together when the second catheter is slidably disposed within the first catheter such that a rotational orientation of the second catheter is fixed relative to a rotational orientation of the first opening,
    wherein the second key joint component and the fourth key joint component are configured to be coupled together when the third catheter is slidably disposed within the first catheter such that a rotational orientation of the third catheter is fixed relative to the rotational orientation of the second opening,
    wherein the pre-formed bend of the second catheter extends at a non-zero angle relative to a longitudinal axis of the first catheter when the second distal end is extended from the lumen of the first catheter, and
    wherein the pre-formed bend of the third catheter extends at a non-zero angle relative to a longitudinal axis of the first catheter when the third distal end is extended from the lumen of the first catheter.

2. The aspiration catheter system of claim 1, wherein the fitting is configured to be selectively coupled to the first elongated body of the first catheter.

3. The aspiration catheter system of claim 1, wherein the first catheter is an endotracheal tube.

4. The aspiration catheter system of claim 1,
    wherein the pre-formed bend of the second catheter is a compound bend that includes:
        a first pre-formed bend that extends at a first non-zero angle relative to a longitudinal axis of the first catheter, and
        a second pre-formed bend that extends at a second non-zero angle relative to the longitudinal axis of the first catheter, and
    wherein the pre-formed bend of the third catheter is a compound bend that includes:
        a first pre-formed bend that extends at a first non-zero angle relative to the longitudinal axis of the first catheter, and
        a second pre-formed bend that extends at a second non-zero angle relative to the longitudinal axis of the first catheter.

5. The aspiration catheter system of claim 1, wherein a direction at which the third distal end extends from the longitudinal axis at the rotational orientation of the third catheter is about 180 degrees rotated from a direction at which the second distal end extends from the longitudinal axis at the rotational orientation of the second catheter.

6. The aspiration catheter system of claim 1 further comprising:
    an antenna having a distal portion disposed on the distal end of the elongated body configured for emitting a signal that can be detected outside a body.

7. The aspiration catheter of claim 6, wherein the distal portion of the antenna comprises a metal band around the elongated body, wherein the antenna further comprises a signal transmission line extending from the metal band to the proximal end.

8. The aspiration catheter of claim 6, wherein the signal is a radio wave.

9. The aspiration catheter system of claim 1, wherein the second lumen is hollow and is configured to transport fluid through the opening proximal to the distal end of the second catheter.

10. The aspiration catheter system of claim 1, wherein the interior of the second lumen of the second catheter is in fluid communication with an exterior of the second catheter through a plurality of openings proximal to the distal end of the second catheter, at least one opening of the plurality of openings being on the distal end, and at least one other opening of the plurality of openings being near the distal end.

* * * * *